United States Patent [19]
Goto et al.

[11] Patent Number: 5,580,883
[45] Date of Patent: Dec. 3, 1996

US005580883A

[54] AMINOBENZENE COMPOUNDS TO PREVENT NERVE CELL DEGRADATION

[75] Inventors: Giichi Goto, Toyono-gun; Hidefumi Yukimasa, Nara; Masaomi Miyamoto, Takarazuka, all of Japan

[73] Assignee: Takeda Chemical Industries, Ltd., Osaka, Japan

[21] Appl. No.: 266,614

[22] Filed: Jun. 28, 1994

Related U.S. Application Data

[63] Continuation of Ser. No. 847,440, Mar. 10, 1992, abandoned, which is a continuation of Ser. No. 674,158, Mar. 25, 1991, abandoned.

[30] Foreign Application Priority Data

Mar. 26, 1990 [JP] Japan ..................................... 2-77178
Jun. 27, 1990 [JP] Japan ................................... 2-169098
Feb. 21, 1991 [JP] Japan ................................... 3-050753

[51] Int. Cl.$^6$ ................... A61K 31/445; A61K 31/44; A61K 31/38; A61K 331/535
[52] U.S. Cl. .................. 514/315; 514/320; 514/318; 514/326; 514/329; 514/336; 514/430; 514/449; 514/450; 514/231.2; 514/304; 514/357
[58] Field of Search ............ 564/304; 514/351, 514/357, 315, 320, 326, 329, 336, 430, 449, 450, 231.2

[56] References Cited

U.S. PATENT DOCUMENTS

| | | | |
|---|---|---|---|
| 3,480,617 | 11/1969 | Farhat et al. | 514/351 X |
| 3,586,655 | 6/1971 | Farhat | 260/458 N |
| 4,310,530 | 1/1982 | Nishiyama et al. | 514/351 |
| 4,317,827 | 3/1982 | Lesher et al. | 514/351 |
| 4,338,326 | 7/1982 | Cain et al. | 514/351 |
| 4,377,585 | 3/1983 | Lesher et al. | 514/351 |

FOREIGN PATENT DOCUMENTS

| | | |
|---|---|---|
| 0229391 | 7/1987 | European Pat. Off. . |
| 0332570 | 9/1989 | European Pat. Off. . |
| 0378207 | 7/1990 | European Pat. Off. . |

OTHER PUBLICATIONS

Chemical Abstracts, vol. 63, 1965, 46–Dyes.
P. Caubere, "Arynic and SnAr Reactions of Polyhalogenobenzenes"–VI12, Tetrahydron., vol. 33, pp. 955–959, Dec. 13, 1976.
A. E. Oberster, et al., "Syntheses of Novel Substituted p–phenylenediamines", Canadian Journal of Chemistry, Feb. 1, 1967, vol. 45, No. 3.

R. K. Grantham et al., "Dihydrobenzimidazole Chemistry. Part IV. Acid–catalysed Reactions of Anils and Dihydrobenzimidazoles", J. Chem. Soc. (C), 1969, pp. 1444–1448.
CA: 72(7): No. 31647g (1970)–Farhat et al.
CA: 75(19): No. 119099c (1971)–Farhat et al.

Primary Examiner—Theodore J. Criares
Attorney, Agent, or Firm—Foley & Lardner

[57] ABSTRACT

A compound useful for central antioxidant having inhibitory activity of degeneration and necrocytosis of cerebral cells of the formula (I):

(I)

$(A)_p$ — benzene ring with substituents $R_4$, B, $R_5$, $R_6$ wherein
A and B are independently (1) a group of the formula:

$$-N\begin{array}{c} R_1 \\ R_2 \end{array}$$

wherein $R_1$ and $R_2$ are independently hydrogen atom, an optionally substituted hydrocarbon residue or an optionally substituted heterocyclic group, or $R_1$ together with $R_2$ and the nitrogen atom to which they are bound may form a cyclic amino group, provided that both $R_1$ and $R_2$ are not hydrogen atom at the same time, or (2) a group of the formula:

$$R_3-N\overbrace{(CH_2)_m}^{\phantom{x}}(CH_2)_n-D-$$

wherein D is O or S, $R_3$ is hydrogen atom, an optionally substituted hydrocarbon residue or an optionally substituted acyl group, m is 1, 2, or 3 and n is 0, 1, 2, 3 or 4;
p is 1 or 2, provided that both A may be the same or different when p is 2; and
$R_4$, $R_5$ and $R_6$ are independently hydrogen atom, a lower alkyl or a lower alkoxy, or $R_5$ and $R_6$ may bond together to form —CH=CH—CH=CH—, or a salt thereof.

4 Claims, No Drawings

AMINOBENZENE COMPOUNDS TO PREVENT NERVE CELL DEGRADATION

This application is a continuation of U.S. application Ser. No. 07/847,440 filed Mar. 10, 1992, now abandoned which is a continuation of U.S. application Ser. No. 07/674,158 filed Mar. 25, 1991 now abandoned.

FIELD OF THE INVENTION

The present invention relates to aminobenzene compounds of the general formulas (I), (II), (III) and (IV) as shown hereinafter or salts thereof, their production and use as central antioxidants.

BACKGROUND OF THE INVENTION

It is considered that glutamic acid and aspattic acid which are stimulative amino acids are responsible for degeneration and necrocytosis of cerebral nerve cells caused by cerebral ischemia due to cerebral infarction, cerebral hemorrhage, suspension of heart beat, operation of the lung, cerebral injury and the like as well as anoxia. However, there are many unclear points in the mechanism thereof. Although a lot of efforts have been made heretofore so as to investigate antagonists of glutamate as the means for inhibiting degeneration and necrocytosis of cerebral nerve cells, any effective and satisfactory medicine has not yet been found out.

OBJECTS OF THE INVENTION

The main object of the present invention is to investigate compounds which can inhibit necrocytosis of cerebral nerve cells caused by addition of glutamic acid and to provide such effective compounds as central antioxidants.

It is considered that the addition of glutamic acid to N-18-RE-105 cell line (Neuroblastoma-primary retina hybrid cells) causes inhibition of incorporation of cystine into cells as well as decrease in accompanying intracellular concentration of glutathione, whereby, oxidative stress of cells, namely, intracellular accumulation of active oxygen and peroxides is taken place, which results in degeneration and necrocytosis [Neuron, 2, 1547 (1989); J. Pharmacol. Exp. Ther., 250, 1132 (1989)].

The present inventors have investigated compounds for inhibiting necrocytosis caused by glutamic acid by employing this evaluation system. As a result, it has been found that compounds of the formula (I) as shown hereinafter have an inhibitory activity of necrocytosis. The present inventors have further studied the compounds and completed the present invention.

SUMMARY OF THE INVENTION

According to the present invention, there is provided a central antioxidant having inhibitory activity of degeneration and necrocytosis of cerebral cells (hereinafter merely referred to as the central antioxidant) comprising as an effective component a compound of the formula (I):

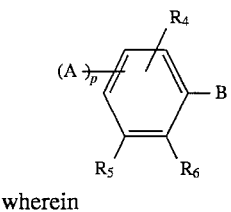
(I)

wherein

A and B are independently (1) a group of the formula:

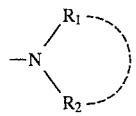

wherein $R_1$ and $R_2$ are independently hydrogen atom, an optionally substituted hydrocarbon residue or an optionally substituted heterocyclic group, or $R_1$ together with $R_2$ and the nitrogen atom to which they are bound may form a cyclic amino group, provided that both $R_1$ and $R_2$ are not hydrogen atom at the same time, or (2) a group of the formula:

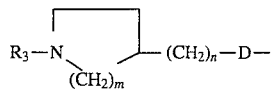

wherein D is O or S, $R_3$ is hydrogen atom, an optionally substituted hydrocarbon residue or an optionally substituted acyl group, m is 1, 2, or 3 and n is 0, 1, 2, 3 or 4;

p is 1 or 2, provided that both A may be the same or different when p is 2; and $R_4$, $R_5$ and $R_6$ are independently hydrogen atom, a lower alkyl or a lower alkoxy, or $R_5$ and $R_6$ may bond together to form —CH=CH—CH=CH—, or a salt thereof.

DETAILED DESCRIPTION OF THE INVENTION

Among the compounds of the formula (I), compounds of the formula (II):

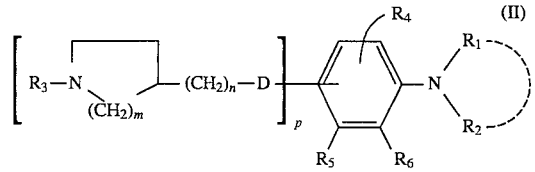
(II)

wherein each symbol is as defined above, or salts thereof; compounds of the formula (III):

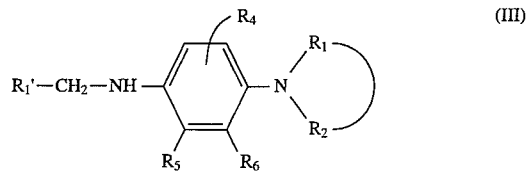
(III)

wherein $R_1'$ is an optionally substituted hydrocarbon residue except an alkyl group having no substituent, and the formula:

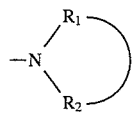

represents a cyclic amino group formed by $R_1$ and $R_2$ together with the nitrogen atom to which they are bound, and the other symbols are as defined above, or salts thereof; and compounds of the formula (IV):

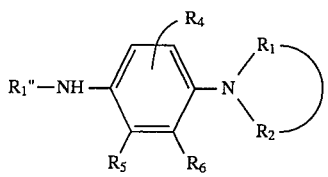
(IV)

wherein $R_1''$ is an optionally substituted heterocyclic group, and the other symbols are as defined above, or salts thereof are novel compounds synthesized by the present inventors. Accordingly, another aspect of the present invention is to provide these novel compounds.

In the above formula (I), as the "hydrocarbon residue" of the "optionally substituted hydrocarbon residue" represented by $R_1$, $R_1'$, $R_2$ and $R_3$, there are, for example, an alkyl group having 1 to 6 carbon atoms (e.g., methyl, ethyl, propyl, butyl, hexyl, 4-methylpentyl, etc.); an alkenyl group having 2 to 4 carbon atoms (e.g., vinyl, allyl 2-butenyl, etc.); an alkynyl group having 2 to 4 carbon atoms (e.g., propargyl, 2-butynyl, etc.); an aryl group having 6 to 12 carbon atoms (e.g., phenyl, naphthyl, etc.); an aralkyl having 7 to 14 carbon atoms (e.g., benzyl, diphenylmethyl, phenylethyl, naphthylmethyl, naphthylethyl, etc.) and the like. The aryl and aralkyl groups in $R_1$, $R_1'$, $R_2$ and $R_3$ may have 1 to 3 substituents on the rings thereof and examples of the substituents include an alkoxy group having 1 to 3 carbon atoms (e.g., methoxy, ethoxy, etc.), an alkyl group having 1 to 3 carbon atoms (e.g., methyl, ethyl, propyl, etc.), cyano group, amino group, mono- or di-$C_{1-6}$ alkylamino group, 5 to 7 membered cyclic amino group (e.g., as described hereinafter with respect to the cyclic amino group formed by $R_1$ and $R_2$ together with the nitrogen atom to which they are bound), hydroxyl group, nitro group, halogen (e.g., chlorine atom, fluorine atom, bromine atom, etc.) and the like.

Further, the above alkyl, alkenyl and alkynyl groups represented by $R_1$, $R_1'$, $R_2$ and $R_3$ may have 1 to 4, preferably 1 to 3 substituents and examples of the substituent include halogen, an alkoxy group having 1 to 3 carbon atoms, cyano group, amino group, mono- or di-$C_{1-6}$ alkylamino group, 5 to 7 membered cyclic amino group (e.g., as described hereinafter with respect to the cyclic amino group formed by $R_1$ and $R_2$ together with the nitrogen atom to which they are bound), hydroxyl group and the like, provided that $R_1'$ is not an unsubstituted alkyl group.

The "heterocyclic group" of the "optionally substituted heterocyclic group" represented by $R_1$, $R_2$ and $R_1''$ is preferably 5 to 8 membered, more preferably, 5 to 6 membered saturated or unsaturated heterocyclic groups containing as ring-constituting atoms 1 to 4, preferably, 1 to 2 hetero atoms selected from the groups consisting of N, O and S. As the heterocyclic group, a nitrogen-containing saturated heterocyclic group such as piperidinyl group, pyrrolidinyl group or the like is particularly preferred. Accordingly, the group represented by the formula:

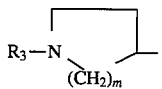

wherein each symbol is as defined above, which is included in the formula (I) and (II), is preferred. Examples of the substituent of the heterocyclic group include those as described above with respect to the hydrocarbon residue.

As the "acyl group" of the "optionally substituted acyl group" represented by $R_3$, there are, for example, a carboxylic acyl group (e.g., an alkyl carbonyl having 2 to 6 carbon atoms such as acetyl, propionyl, butyryl, etc.); a substituted oxycarbonyl group (e.g., alkyl- or aralkyloxycarbonyl having 2 to 8 carbon atoms such as methyloxycarbonyl, tert-butyloxycarbonyl, benzyloxycarbonyl, etc.); a substituted aminocarbonyl group (e.g., alkyl- or dialkylaminocarbonyl having 1 to 4 carbon atoms such as methylaminocarbonyl, ethylaminocarbonyl, dimethylaminocarbonyl, diethylaminocarbonyl, etc.) and the like.

Examples of the substituent which is optionally contained in the acyl group include halogen (e.g., iodine, bromine, fluorine, chlorine, etc.), amino group, primary or secondary amino group having an alkyl group having 1 to 6 carbon atoms (e.g., methyl, ethyl, propyl, hexyl, etc.) and the like. The acyl group may have 1 to 3, preferably, 1 to 2 substituents.

As the "cyclic amino group formed by $R_1$ and $R_2$ together with the nitrogen to which they are bound", there are a nitrogen-containing 5 to 7 membered heterocyclic group and a nitrogen-containing 5 to 7 membered heterocyclic group fused to benzene ring. Examples thereof include a group of the formulas:

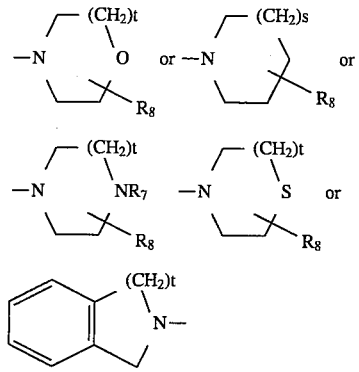

wherein s is 0, 1 or 2; t is 1 or 2; $R_7$ is hydrogen atom or a lower alkyl group having 1 to 6 carbon atoms (e.g., methyl, ethyl, propyl, butyl, hexyl, etc.); and $R_8$ is a substituent which is optionally contained in the cyclic amino group formed by $R_1$ and $R_2$ or hydrogen atom; and examples of the substituent include an alkyl group having 1 to 3 carbon atoms (e.g., methyl, ethyl, propyl, etc.), an alkylcarbonyl group having 1 to 3 carbon atoms (e.g., acetyl, propionyl, butyryl, etc,), oxo, hydroxy group, phenyl group, benzyl group, diphenylmethyl group, amino group and the like.

Examples of the lower alkyl group represented by $R_4$, $R_5$, $R_6$ and $R_7$ include $C_{1-6}$ alkyl group as described above with respect to $R_1$ and the like, and examples of the lower alkoxy group include $C_{1-6}$ alkoxy group represented by $R_4$, $R_5$ and $R_6$ include similar $C_{1-6}$ alkyl containing $C_{1-6}$ alkyl. When p is 2, both A may be the same or different.

When A is a group represented by the formula:

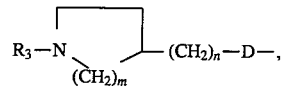

p is preferably 1 or 2 and, when A is a group represented by the formula:

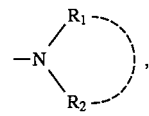

p is preferably 1.

Among the compounds represented by the above (I), the compound wherein A and B are

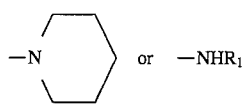

(wherein $R_1$ is $C_{1-6}$ alkyl group, particularly $C_6$ alkyl group) is particularly preferred. Further, the compound wherein A is

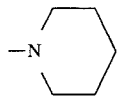

and B is —$(CH_3)_2CH(CH_2)_3$ is particularly superior in the pharmacological activity as described hereinafter.

Examples of a preferred embodiment of the compounds of the above formula (II) include the following compounds.

$R_1$ and $R_2$ are preferably an alkyl group having 1 to 4 carbon atoms, phenylmethyl group, or $R_1$ and $R_2$ together with the nitrogen atom to which they are bound form a cyclic amino group. More preferably, $R_1$ and $R_2$ are an alkyl group having 1 to 3 carbon atoms or $R_1$ and $R_2$ together with the nitrogen atom to which they are bound form a group of the formula:

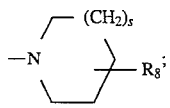

s is 0, 1 or 2; $R_8$ is hydrogen atom, phenyl group or benzyl group. Preferably, $R_3$ is hydrogen atom, an alkyl group having 1 to 4 carbon atoms; m is 1 or 2, particularly 2; and n is 0 or 1, particularly 0.

Examples of another preferred embodiment of the compounds represented by the above formula (II) include the compounds wherein D is O, n is 0, and m is 2; and $R_3$ is hydrogen or alkyl having 1 to 7 carbon atoms, particularly hydrogen or alkyl having 1 to 4 carbon atoms. As the group

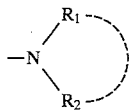

of the compound (II),

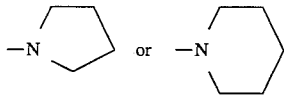

is preferred.

Examples of the preferred embodiment of the compounds of the above formula (III) include the following compounds.

In view of the pharmacological activity, $R_1'$ is preferably alkyl group having 3 to 7 carbon atoms or cycloalkyl group and the group

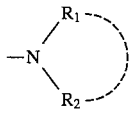

is preferably

Examples of the preferred embodiment of the compounds of the above formula (IV) include the compounds wherein

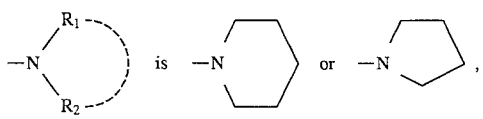

and $R_1''$ is

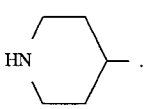

In the compounds of the formulas (I) to (IV), $R_4$, $R_5$ and $R_6$ are preferably hydrogen atom or an alkyl group having 1 to 3 carbon atoms.

In the present invention, the compounds (I), (II), (III) and (IV) may form their acid addition salts, particularly, physiologically acceptable acid addition salts, and examples of the salts include those formed with inorganic acids (e.g., hydrochloric acid, sulfuric acid, nitric acid, phosphoric acid, hydrobromic acid, etc.), and organic acids (e.g., acetic acid, propionic acid, fumaric acid, maleic acid, tartaric acid, citric acid, malic acid, oxalic acid, benzoic acid, methanesulfonic acid, benzenesulfonic acid, etc.).

The process for the production of the compounds of the present invention will be explained hereinafter.

A part of the compounds represented by the above formula (I) are, for example, known compounds described in U.S. Pat. Nos. 3,480,617 and 3,586,655; Canadian Journal of Chemistry, 45, 195 (1967); Tetrahedron, 33, 955 (1977), and these compounds of the formula (I) can be synthesized according to the methods described in the above references or modifications thereof.

On the other hand, among the compounds represented by the formula (I) of the present invention, the compounds represented by the formula (II) are novel compounds as described above and, for example, they can also be produced by the following method. Among the compounds of the formula (II), compounds represented by the formula (Ia):

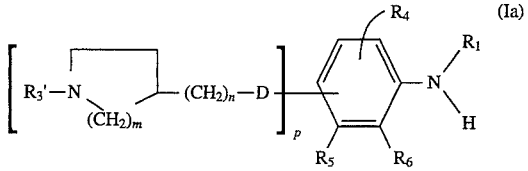

wherein $R_3'$ is an optionally substituted acyl group as defined in $R_3$ and the other symbols are as defined above (hereinafter, merely referred to as the "compound (Ia)") can be obtained, for example, by reacting a compound represented by the formula (II'):

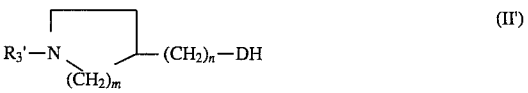

wherein each symbol is as defined above with a compound represented by the formula (II''):

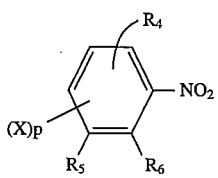 (II")

wherein X is halogen (e.g., fluorine, chlorine, bromine, iodine, etc.) and the other symbols are as defined above to form a compound represented by the formula (V):

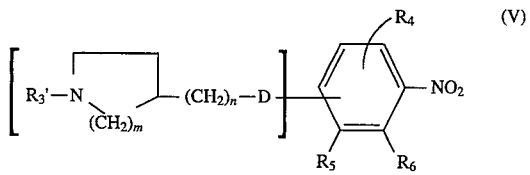 (V)

wherein each symbol is as defined above; reducing the compound (V) to obtain a compound represented by the formula (V'):

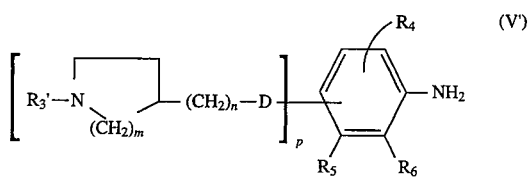 (V')

wherein each symbol is as defined above; and then reacting the compound (V') with a compound represented by the formula (VI):

 (VI)

$R_1$—X wherein $R_1$ is as defined above and X is halogen (e.g., bromine, chlorine, iodine, etc).

Further, the compound represented by the formula (Ia) can also be obtained by reacting the compound represented by the formula (V') with a compound represented by the formula (VII):

$R_1''$—CHO (VII)

wherein $R_1''$ is such "an optionally substituted hydrocarbon residue" that $R_1''CH_2$ becomes the same as $R_1$.

The reaction of the compound represented by the formula (II') with the compound represented by the formula (II") can be conducted according to a known method. For example, the reaction can be conducted in the absence of a solvent, or in a solvent, at a temperature of −50° to 300° C., preferably 20° to 200° C. The solvent may be any solvent which is normally used, and examples thereof include water, methanol, ethanol, propanol, chloroform, dichloromethane, benzene, toluene, xylene, acetonitrile, dimethylformamide, N-methylpyrrolidone, dimethylsulfoxide and the like. If necessary, the reaction can be conducted, for example, in the presence of an organic base such as pyridine, 4-dimethylaminopyridine, triethylamine, triethylenediamine, tetramethylethylenediamine, etc.; an inorganic base such as sodium bicarbonate, potassium bicarbonate, sodium carbonate, potassium carbonate, sodium hydroxide, potassium hydroxide, etc.; sodium hydride; potassium hydride or the like. The compound represented by the formula (II") is normally used in an amount of about 1 to 3 moles, preferably 1 to 1.5 moles per 1 mole of the compound represented by the formula (II'). Further, the reaction time is normally about 0.5 to 24 hours, preferably 2 to 10 hours.

In a known method for reducing the compound represented by the formula (V), as a solvent, any solvent which is normally used in the chemical reaction can be used in so far as it does not interfere with the reaction. For example, the reaction can be conducted in a solvent such as water, methanol, ethanol, dimethylformamide, tetrahydrofuran, dioxane or the like in the presence of a catalyst such as palladium, rhodium, platinum, raney nickel or the like, at about −10° to 100° C., preferably 20° to 50° C., under hydrogen pressure of 1 to 100 atm, preferably 1 to 5 atm, if necessary, in the presence of an acid. Examples of the acid to be used include inorganic acids (e.g., hydrochloric acid, nitric acid, phosphoric acid, hydrobromic acid) or organic acids (e.g., acetic acid, propionic acid, tartric acid, benzoic acid, methanesulfonic acid, toluenesulfonic acid, etc.) and the like.

The reaction of the compound represented by the formula (V') with the compound represented by the formula (VI) can also be conducted according to a known method. For example, the reaction can be conducted in a solvent, at a temperature of about 20° to 200° C., preferably 50° to 100° C. The solvent can be any one which is normally used, and examples thereof include water, methanol, ethanol, propanol, chloroform, dichloromethane, benzene, toluene, xylene, acetonitrile, dimethylformamide, N-methylpyrrolidone, dimethylsulfoxide and the like. If necessary, the reaction can be conducted, for example, in the presence of an inorganic base such as sodium bicarbonate, potassium bicarbonate, sodium carbonate, potassium carbonate, sodium hydroxide, potassium hydroxide or the like.

The compound represented by the formula (VI) is normally used in an amount of about 0.3 to 2 moles, preferably 0.5 to 1 moles per 1 mole of the compound represented by the formula (V'). Further, the reaction time is normally about 1 to 48 hours, preferably about 10 to 20 hours.

The reaction of the compound represented by the formula (V') with the compound represented by the formula (VII) can be conducted by subjecting to reductive amination in a solvent such as methanol, ethanol, propanol or the like by using sodium cyano borohydride. The compound represented by the formula (VII) is normally used in an amount of about 0.5 to 10 moles, preferably 1 to 2 moles per 1 mole of the compound represented by the formula (V'). The reaction time is normally about 1 to 2 hours, preferably about 2 to 5 hours.

Among the compounds (II), compounds represented by the formula (Ib):

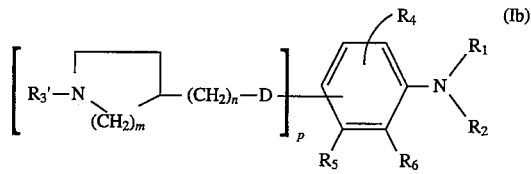 (Ib)

wherein each symbol is as defined above can be obtained by reacting the compound represented by the above formula (Ia) with a compound of the formula (VIII):

$R_2$—X (VIII)

wherein $R_2$ is as defined above and X is halogen (e.g., bromine, chlorine, iodine, etc.), or a compound of the formula (IX):

$R_2'$—CHO (IX)

wherein $R_2'$ is such "an optionally substituted hydrocarbon residue" that $R_2'CH_2$ become the same group as that of $R_2$, under the same conditions as those in the reaction of the compounds of the above formulas (V') and (VI) or the compounds of the formulas (V') and (VII). Further, the compound of the formula (Ib) can be obtained by reacting the compound of the formula (V') with the compound of the formula (VI) or (VII). In this case, $R_1$ and $R_2$ are hydrocarbon residues which may have the same substituents.

Further, the compound of the formula (Ib) can be obtained by reacting the compound of the formula (V') with a compound of the formula (X):

$$PO(OR_9)_3 \qquad (X)$$

wherein $R_9$ is an alkyl group having 1 to 6 carbon atoms in the absence of a solvent, or in a solvent, at a temperature of about 100° to 300° C., preferably 150° to 200° C. Examples of the solvent include dimethylformamide, N-methylpyrrolidone, dimethylsulfoxide and the like. The compound represented by the formula (X) is normally used in an amount of about 1 to 3 moles, preferably about 1 to 1.5 moles per 1 mole of the compound represented by the formula (V'). The reaction time is normally about 1 to 10 hours, preferably 3 to 5 hours.

Among the compounds (II), compounds represented by the formula (Ic):

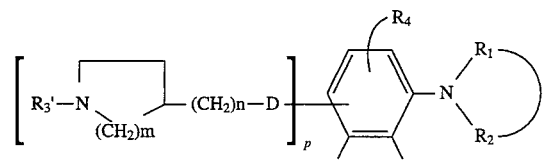

wherein each symbol is as defined above, provided that

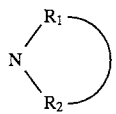

is as defined above and, among

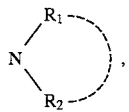

the cyclic amino group formed together with the nitrogen atom to which $R_1$ and $R_2$ are bound group, can be obtained by reacting the compound of the formula (V') with a compound represented by the formula (XI):

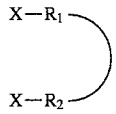

wherein X is halogen (e.g., bromine, chlorine, iodine, etc.)

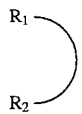

is a group corresponding to the above

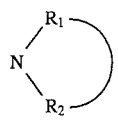

wherein N is removed therefrom.

The reaction of the compound represented by the formula (V') with the compound represented by the formula (XI) can be conducted according to a known method. For example, the reaction can be conducted in the absence of a solvent, or in a solvent, at a temperature of about −50° to 300° C., preferably 20° to 200° C. The solvent can be any one which is normally used and examples thereof include water, methanol, ethanol, propanol, chloroform, dichloromethane, benzene, toluene, xylene, acetonitrile, dimethylformamide, N-methylpyrrolidone, dimethylsulfoxide and the like. If necessary, the reaction can be conducted, for example, in the presence of an organic base such as pyridine, 4-dimethylaminopyridine, triethylamine, triethylenediamine, tetramethylethylenediamine, etc.; an inorganic base such as sodium bicarbonate, potassium bicarbonate, sodium carbonate, potassium carbonate, sodium hydroxide, potassium hydroxide, etc.; sodium hydride; potassium hydride or the like. The compound represented by the formula (I) is normally used in an amount of about 0.1 to 3 moles, preferably 0.5 to 1 moles per 1 mole of the compound represented by the formula (V'). The reaction time is normally about 1 to 48 hours, preferably 3 to 20 hours.

Among the compounds (II), compounds represented by the formula (Id):

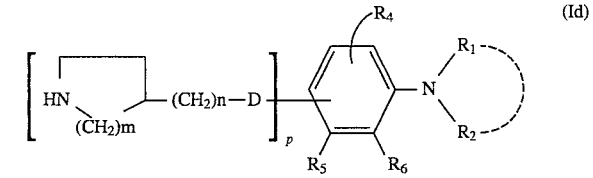

wherein each symbol is as defined above can be obtained by subjecting the compound represented by the formula (Ia), (Ib) or (Ic) to deacylation reaction in an aqueous solution of a mineral acid (e.g., nitric acid, hydrochloric acid, hydrobromic acid, iodic acid, sulfuric acid, etc.) or an alkali hydroxide (e.g., sodium hydroxide, potassium hydroxide, barium hydroxide, lithium hydroxide, etc.), at 10° to 150° C., preferably 50° to 100° C. The acid or base is normally used in an amount of about 10 to 100 equivalent amounts, preferably 20 to 40 equivalent amounts per 1 mole of the compound of the formula (Ia), (Ib) or (Ic). The strength of the acid or base is preferably about 1 to 10N, preferably 4 to 10N. The reaction time is varied according to the reaction temperature and is normally about 1 to 24 hours, preferably 2 to 10 hours.

Among the compounds (II), compounds represented by the formula (Ie):

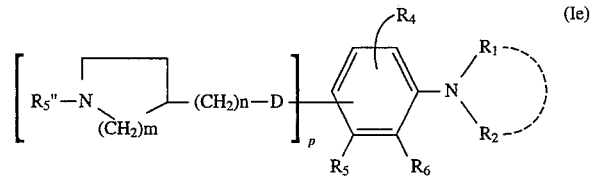

wherein $R_3''$ is $R_3$ other than hydrogen atom, namely, "an optionally substituted hydrocarbon residue" and "an optionally substituted acyl group" and the other symbols are as defined above can be obtained by reacting the compound represented by the formula (Id) with a compound represented by the formula (XII):

$$R_3''-X \quad (XII)$$

wherein $R_3''$ is as defined above and X is halogen (e.g., bromine, chlorine, iodine, etc.). In the reaction, the solvent to be used can be any one which is normally used. For example, the reaction can be conducted in a protic solvent (e.g., water, methanol, ethanol, propanol, etc.) or an aprotic solvent (e.g., ethyl ether, tetrahydrofuran, dioxane, dimethylformamide, acetonitrile, etc.), at −10° to 200° C., preferably 20° to 100° C.

If necessary, this reaction can be conducted, for example, in the presence of an organic base such as pyridine, 4-dimethylaminopyridine, triethylamine, triethylenediamine, tetramethylethylenediamine, etc.; an inorganic base such as sodium bicarbonate, potassium bicarbonate, sodium carbonate, potassium carbonate, sodium hydroxide, potassium hydroxide, etc.; sodium hydride; potassium hydride or the like.

The compound represented by the formula (XII) is normally used in an amount of about 1 to 10 moles, preferably 1 to 2 moles per 1 mole of the compound represented by the formula (Id). The reaction time is normally about 1 to 48 hours, preferably 1 to 10 hours.

Among the objective compounds represented by the formula (II) according to the present invention, compound represented by the formula (If):

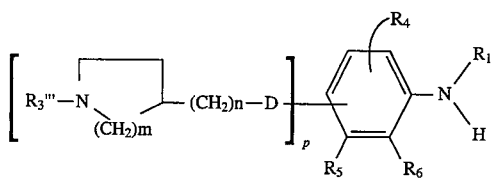

wherein $R_3'''$ is, among the group of $R_3$, "an optionally substituted hydrocarbon residue" and the other symbols are as defined above can be obtained, for example, by reacting a compound represented by the formula (XIII):

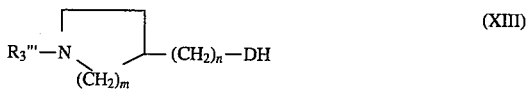

wherein each symbol is as defined above with the compound represented by the formula (II″) under the same reaction conditions as those of the reaction of the above compounds (I′) and (II′) to form a compound represented by the formula (XIV):

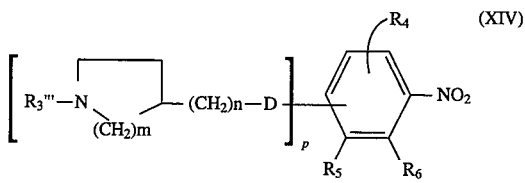

wherein each symbol is as defined above; converting the compound (XIV) into a compound represented by the formula (XV):

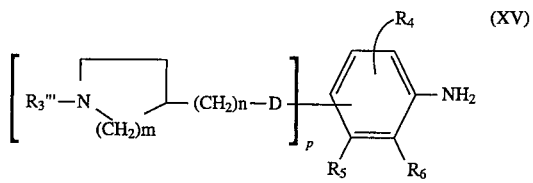

wherein each symbol is as defined above under the same reaction conditions as those of conversion of the compound of the formula (V) into the compound of the formula (V′); reacting the compound (XV) with a compound represented by the formula (XVI):

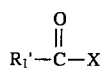

wherein $R_1'$ is as defined above and X is halogen (e.g., bromine, chlorine, iodine, etc.) to form a compound represented by the formula (XVII):

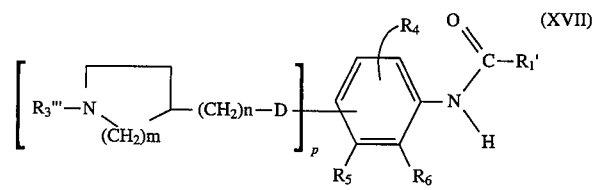

wherein each symbol is as defined above; and then reducing the compound (XVII).

The reaction of the compound represented by the formula (XV) with the compound of the (XVI) is a know reaction and, for example, can be conducted by reacting the compound represented by the formula (XV) with the compound of the (XVI) in the absence of a solvent, or in a solvent, at a temperature of about −50° to 100° C., preferably 20° to 50° C. The solvent to be used can be any one which is normally used, and examples thereof include water, chloroform, dichloromethane, benzene, toluene xylene, acetonitrile, dimethylformamide, N-methylpyrrolidone, dimethylsulfoxide and the like. If necessary, this reaction can be conducted, for example, in the presence of an organic base such as pyridine, 4-dimethylaminopyridine, triethylamine, triethylenediamine, tetramethylethylenediamine, etc.; an inorganic base such as sodium bicarbonate, potassium bicarbonate, sodium carbonate, potassium carbonate, sodium hydroxide, potassium hydroxide, etc.; sodium hydride; potassium hydride or the like.

The compound represented by the formula (XVI) is normally used in an amount of about 1 to 10 moles, preferably 1.5 to 4 moles per 1 mole of the compound represented by the formula (XV). The reaction time is normally about 1 to 48 hours, preferably about 2 to 10 hours. The reduction of the compound of the formula (XVII) can be conducted in a solvent by treating it with a metallic hydride (e.g., diisobutylaluminum hydride, triphenyltin hydride, etc.) or a metallic hydrogen complex (e.g., lithium aluminum hydride, sodium aluminum hydride, sodium triethoxyaluminum hydride, etc.). In this reaction, the solvent to be used can be any one which is normally used in so far as it does not interfere with the reaction, for example, the reaction can be conducted in a protic solvent (e.g., water, methanol, ethanol, propanol, etc.) or an aprotic solvent (e.g., ethyl ether, tetrahydrofuran, dioxane, etc.), at −10° to 200° C., preferably 20° to 100° C.

Among the compounds represented by the formula (II), compound represented by the formula (Ig):

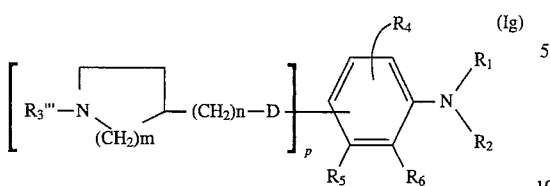

wherein each symbol is as defined above can be obtained, for example, by reacting the compound represented by the formula (If) with a compound represented by the formula (XVIII):

wherein each symbol is as defined above and X is halogen (e.g., bromine, chlorine, iodine, etc.) under the same reaction conditions as those of the reaction of the compounds of the above formulas (XV) and (XVI) to form a compound represented by the formula (XIX):

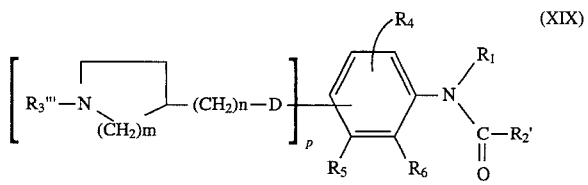

wherein each symbol is as defined above; reducing the compound (XIX) under the same conditions as those for reducing the compound of the formula (XVII) to the compound of the formula (If).

Among the compounds represented by the formula (I), the compounds represented by the formula (III) is also novel compounds. The compounds (III) can be produced by a known method. Further, the compounds (III) can also be produced according to the following method. Namely, it can be obtained by reacting a compound represented by the formula (XX):

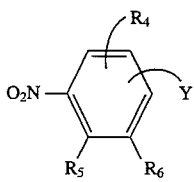

wherein Y is halogen (e.g., fluorine, chlorine, bromine, iodine, etc.) with a compound represented by the formula (XXI):

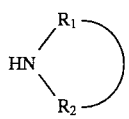

wherein each symbol is as defined above to form a compound represented by the formula (XXII):

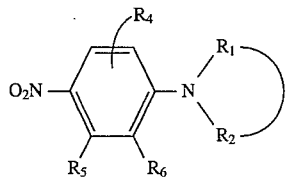

wherein each symbol is as defined above; converting the resulting compound into a compound represented by the formula (XXIII):

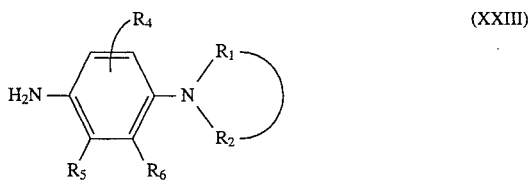

wherein each symbol is as defined above; reacting the latter compound with a compound represented by the formula (XXIV):

$$R_1'\text{—}CH_2\text{—}Y \qquad \text{(XXXIV)}$$

wherein each symbol is as defined above, or a compound represented by the formula (XXV):

$$R_1'\text{—}CHO \qquad \text{(XXV)}$$

wherein $R_1'$ is as defined above, or a compound represented by the formula (XXVI):

wherein each symbol is as defined above, to form a compound represented by the formula (XXVII):

wherein each symbol is as defined above; and then reducing the resulting compound.

The reaction of the compound represented by the formula (XX) with the compound represented by the formula (XXI) does not necessarily require a solvent. However, in the case of using a solvent, it is preferred to use a hydrocarbon solvent (e.g., pentane, hexane, benzene, toluene, etc.); a halogenohydrocarbon solvents (e.g., dichloromethane, chloroform, dichloroethane, carbon tetrachloride, etc.); an ether solvent (e.g., ethyl ether, tetrahydrofuran, dioxane, dimethoxyethane, etc.); an amido solvent (e.g., dimethylformamide, hexamethylphosphonotriamide, etc.); dimethylsulfoxide or the like, normally. The reaction can be conducted at $-10°$ to $200°$ C., preferably $0°$ to $50°$ C.

The compound represented by the formula (XXI) is used in an amount of about 1 to 20 equivalent amounts, preferably 1 to 4 equivalent amounts per 1 equivalent of the compound represented by the formula (XX). The reaction time is varied according to the reaction temperature and is normally about 1 to 24 hours, preferably 2 to 20 hours. This reaction can be conducted, for example, in the presence of an inorganic base such as sodium bicarbonate, potassium bicarbonate, sodium carbonate, potassium carbonate, sodium hydroxide, potassium hydroxide, etc., sodium hydride, potassium hydride, n-butyllithium or the like.

The conversion of the compound represented by the formula (XX) into the compound represented by the formula (XXI) can be conducted according to a known method for converting nitro group of the compound represented by the formula (XXII) into amino group. Namely, the compound represented by the formula (XXII) can be produced by catalytic hydrogenation reduction thereof in a solvent in the presence of a catalyst. The solvent to be used can be any one which is normally used in chemical reactions in so far as it does not interfere with the reaction. For example, the reaction can be conducted in a solvent such as water, methanol, ethanol, dimethylformamide, tetrahydrofuran, dioxane, etc., in the presence of a catalyst such as palladium, rhodium, platinum, raney nickel, etc., at $-10°$ to $100°$ C., preferably about $20°$ to $50°$ C., under pressure of hydrogen of 1 to 100 atm, preferably 1 to 5 atm and, if necessary, in the presence of a acid. Examples of the acid to be used include mineral acids (e.g., hydrochloric acid, nitric acid, phosphoric acid, hydrobromic acid, etc.) or organic acids (e.g., acetic acid, propionic acid, tartaric acid, benzoic acid, methanesulfonic acid, toluenesulfonic acid, etc.) and the like.

In the reaction of the compound represented by the formula (XXIII) with the compound represented by the formula (XXIV), any solvent which is normally used in chemical reaction can be used in so far as it does not interfere with the reaction. For example, the reaction can be conducted in a protic solvent (e.g., water, methanol, ethanol, propanol, etc.) or an aprotic solvent (e.g., ethyl ether, tetrahydrofuran, dioxane, dimethylformamide, acetonitrile, etc.), at a temperature of $-10°$ to $200°$ C., preferably $20°$ to $100°$ C.

If necessary, the reaction can be conducted, for example, in the presence of an organic base such as pyridine, 4-dimethylaminopyridine, triethylamine, triethylenediamine, tetramethylethylenediamine, etc.; an inorganic base such as sodium bicarbonate, potassium bicarbonate, sodium carbonate, potassium carbonate, sodium hydroxide, potassium hydroxide, etc.; sodium hydride, potassium hydride or the like.

The compound represented by the formula (XXIV) is normally used in an amount of about 1 to 5 moles, preferably 1 to 2 moles per 1 mole of the compound represented by the formula (XXIII). The reaction time is normally about 1 to 48 hours, preferably 1 to 10 hours.

In the reaction of the compound represented by the formula (XXI) with the compound represented by the formula (XXV), the solvent to be used can be any one which is normally used in the chemical reaction in so far as it does not interfere with the reaction. For example, the reaction can be normally conducted by reducing with lithium cyano borohydride, lithium aluminum hydride, diborane, etc. in a solvent such as water, methanol, ethanol, propanol, etc. The reaction temperature is $-30°$ to $100°$ C., preferably $10°$ to $30°$ C. The compound represented by the formula (XXV) is normally used in an amount of 1 to 10 moles, preferably 1 to 2 moles per 1 mole of the compound represented by the formula (XXIII). Further, the reaction time is normally about 0.5 to 10 hours, preferably 1 to 4 hours.

In the reaction of the compound represented by the formula (XXIII) with the compound represented by the formula (XXVI), it is preferred to use a hydrocarbon solvent (e.g., pentane, hexane, benzene, toluene, etc.); a halogenohydrocarbon solvent (e.g., dichloromethane, chloroform, dichloroethane, carbon tetrachloride, etc.); an ether solvent (e.g., ethyl ether, tetrahydrofuran, dioxane, dimethoxyethane, etc.); an amide solvent (e.g., dimethylformamide, hexamethylphosphonotriamide, etc.); dimethylsulfoxide or the like. The reaction can be conducted at $-10°$ to $100°$ C., preferably $10°$ to $40°$ C. If necessary, this reaction can be conducted, for example, in the presence of an organic base such as pyridine, 4-dimethylaminopyridine, triethylamine, triethylenediamine, tetramethylethylenediamine, etc.; an inorganic base such as sodium bicarbonate, potassium bicarbonate, sodium carbonate, potassium carbonate, sodium hydroxide, potassium hydroxide, etc.; sodium hydride, potassium hydride, n-butyllithium or the like.

The compound represented by the formula (XXVI) is normally used in an amount of about 1 to 5 moles, preferably 1 to 2 moles per 1 mole of the compound represented by the formula (XXIII).

The reduction of the compound represented by the formula (XXVII) can be conducted by a known method in a hydrocarbon solvent (e.g., pentane, hexane, toluene, etc.), a halogen solvent (e.g., dichloromethane, chloroform, dichloroethane, etc.), or preferably an ether solvent (e.g., diethyl ether, dipropyl ether, tetrahydrofuran, dioxane, etc.), at a reaction temperature of $-30°$ to $200°$ C., preferably $0°$ to $60°$ C. by using lithium aluminum hydride, sodium aluminum hydride, etc.

Among the compounds represented by the formula (IV), compounds wherein $R_1''$ is a group represented by the above formula:

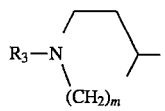

wherein each symbol is as defined above, namely, the compound represented by the formula:

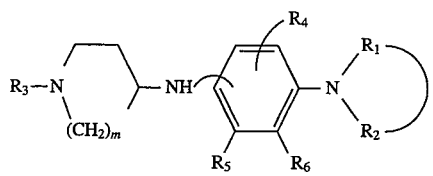

wherein each symbol is as defined above can be produced, for example, by reacting the compound represented by the formula (XXIII) with a compound represented by the formula (XXVIII):

 (XXVIII)

wherein each symbol is as defined above. As the solvent to be used can be any one which is normally used in chemical reactions in so far as it does not interfere with the reaction and, normally, the above compound can be produced by reducing with sodium cyano borohydride, lithium aluminum hydride, diborane, etc. in a solvent such as water, methanol, ethanol, propanol, etc. The reaction temperature is $-30°$ to $100°$ C., preferably $10°$ to $30°$ C. The compound represented by the formula (XXVIII) is normally used in an amount of 1 to 10 moles, preferably 1 to 2 moles per 1 mole of the compound represented by the formula (XXIII). The reaction time is normally about 0.5 to 10 hours, preferably 1 to 4 hours.

The compounds represented by the formula (IV) can be produced modification of the above method or a known method.

When the objective products thus obtained are in the free form, they can be converted into acid addition salts according to a conventional method. On the other hand, when the objective products obtained are in the form of salts, they can be converted into the free form according to a conventional technique.

The reaction product can be isolated and purified by conventional means such as solvent extraction, change of solvent properties, transfer to another solvent, salting-out, crystallization, recrystallization, chromatography and the like.

It has been found that the compounds (I), (II), (III) and (IV) of the present invention (hereinafter generically referred to as the "compounds (I)") show cerebral nerve cell protective activity and central antioxidation activity useful for inhibiting degeneration and necrocytosis of cerebral nerve cell in various symptoms accompanied by intracerebral anoxia and cerebral ischemia, various symptoms accompanied by head injury and various symptoms upon operations by inhibiting accumulation of active oxygen and peroxides in cells, and they can be used for preventing and treating diseases caused by active oxygen and peroxides in cells.

When the compounds (I) are used for preventing and treating the above symptoms, they can be used as they are. However, normally, the compounds (I) are orally or parenterally administered in the form of pharmaceutical compositions combined with known pharmaceutically acceptable carriers.

Dosage forms of the pharmaceutical compositions are not specifically limited and examples thereof include tablets, powder, granules, capsules, injection preparations, suppositories and the like.

The pharmaceutical compositions of the compounds (I) or salts thereof can be prepared according to a conventional method. As carriers for oral preparations, materials which are normally used in the pharmaceutical field, for example, starch, mannit, crystalline cellulose, sodium carboxymethylcellulose and the like can be used. As carriers for injection preparations, distilled water, saline, glucose solution, transfusion and the like can be used.

The dosage of the compounds (I) of the present invention or salts thereof is varied according to a kind of particular diseases, symptoms, age and body weight of patients and the like. However, for a adult patient, in the case of administration by injection, a daily dosage is preferably 0.1 to 3 mg, more preferably 3 to 50 mg. In the case of oral administration, a daily dose is preferably 1 mg to 1 g, more preferably 10 to 300 mg.

As described hereinabove, the compounds (I) and salts thereof are useful as medicines for protecting cerebral nerve cells as well as central antioxidants and they can be used for prevention or treatment of, for example, various symptoms caused by cerebral ischemia due to cerebral infarction, cerebral hemorrhage, suspension of heart beat, operation of the lung or cerebral injury, various symptoms caused by anoxia, various symptoms accompanied by elevation of intracranial pressure due to intracerebral neoplasm and injury pressure, cerebral edema, dementia and the like. Particularly, according to the present invention, there is provided medicines useful for treating cerebral hemorrhage sequela, more particularly, medicines for protecting cerebral nerve cells as well as central antioxidants.

The following Examples, Preparations and Experiment further illustrate the present invention in detail but are not to be construed to limit the scope thereof.

EXAMPLE 1

1-Acetyl-4-(4-pyrrolidinophenyloxy)piperidine

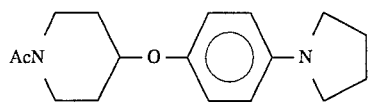

(1) 1-Acetyl-4-hydroxypiperidine (3.7 g) was dissolved in dimethylformamide (20 ml) and to the solution was added sodium hydride (oily, 60 %, 1.04 g), followed by stirring at room temperature for 30 minutes. Then, p-fluoronitrobenzene (2.8 ml) was added dropwise, followed by stirring at room temperature for 30 minutes. Water (50 ml) was added to the mixture and the mixture was extracted with ethyl acetate. The extract was dried over anhydrous magnesium sulfate and the solvent was distilled off. The residue was separated and purified by silica gel column chromatography (developing solvent: ethyl acetate) and then recrystallized from ethyl acetate/ethyl ether to obtain pale yellow crystals (5.5 g), m.p. 91°–92° C.

(2) 1-Acetyl-4-(4-nitrophenyloxy) piperidine (4.72 g) was dissolved in ethanol (50 ml) and to the mixture was added conc. hydrochloric acid (2.5 ml). By using 10% palladium/carbon as a catalyst, catalytic reduction was conducted at a normal temperature and normal pressure. After completion of the reaction, the catalyst was removed and the solvent was distilled off. To the residual oily compound was added water (20 ml). The solution was made basic with addition of solid potassium carbonate and extracted with ethyl acetate. After drying over anhydrous magnesium sulfate, the solvent was distilled off to obtain an oily compound of 1-acetyl-4-(4-aminophenyloxy) piperidine (3.9 g). The oily compound (1.77 g) was dissolved in dimethylformamide (10 ml) and to the mixture were added potassium carbonate (2.1 g) and 1,4-dibromobutane (0.9 ml), followed by heating with stirring at 100° C. for one hour. After completion of the reaction, water (50 ml) was added to the reaction mixture and the mixture was extracted with ethyl acetate. The extract was dried over anhydrous magnesium sulfate and then the solvent was distilled off. The residual oily compound was separated and purified by silica gel column chromatography and then recrystallized from ethyl acetate/ethyl ether to obtain colorless crystals (1.5 g), m.p. 69°–70° C.

Elemental analysis, Calcd. for $C_{17}H_{24}N_2O_2$: C, 70.80; H, 8.39; N, 9.71 Found: C, 70.63; H, 8.61; N, 9.70

EXAMPLE 2

1-Acetyl-4-(4-morpholinophenyloxy)piperidine

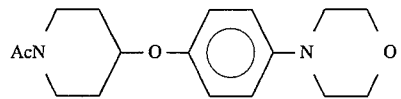

1-Acetyl-4-(4-aminophenyloxy)piperidine (1.77 g) obtained in Example 1 was dissolved in dimethylformamide (10 ml) and to the mixture were added potassium carbonate (2.1 g), potassium iodide (0.2 g) and 2,2'-dichloroethyl ether (0.9 ml), followed by heating with stirring at 100° C. overnight. The mixture was worked up according to the same manner as that described in Example 1 to obtain a colorless oily compound (1.4 g).

Elemental analysis, Calcd. for $C_{17}H_{24}N_2O_3$: C, 67.08; H, 7.95; N, 9.20 Found: C, 66.83; H, 7.86; N, 9.17

NMR (CDCl$_3$) δ: 1.5–2.0 (4H, m), 2.12 (3H, s), 3.0–3.2 (4H, m), 3.2–3.9 (4H, m), 3.75–3.95 (4H, m), 4.2–4.6 (1H, m), 6.86 (4H, s)

EXAMPLE 3

1-Acetyl-4-(4-isoindolynophenyloxy)piperidine

1-Acetyl-4-(4-aminophenyloxy)piperidine (0.94 g) obtained in Example 1 was dissolved in dimethylformamide (10 ml) and to the mixture were added potassium carbonate (1.1 g) and α, α′-dibromo-o-xylene (1.06 g), followed by heating with stirring at 100° C. for one hour. The mixture was worked up according to the same manner as that described in Example 1 to obtain a solid and it was recrystallized from ethanol/ethyl acetate to obtain colorless crystals (1.1 g), m.p. 198°–199° C.

Elemental analysis, Calcd. for $C_{21}H_{24}N_2O_2$: C, 74.97; H, 7.19; N, 8.33 Found: C, 74.75; H, 7.02; N, 8.32

EXAMPLE 4

1-Acetyl-4-(4-dimethylaminophenyloxy)piperidine

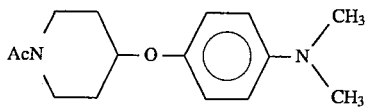

To 1-acetyl-4-(4-aminophenyloxy)piperidine (2.34 g) obtained in Example 1 was added trimethyl phosphate (1.17 ml), followed by heating with stirring at 200° C. for 2 hours. To the mixture were added water (10 ml) and sodium hydroxide (1.5 g) and the mixture was stirred at room temperature for additional 2 hours. After extraction with ethyl acetate, the extract was dried over anhydrous magnesium sulfate and then the solvent was distilled off. The residue was separated and purified by silica gel column chromatography (developing solvent: ethyl acetate). The solid thus obtained was recrystallized from ethyl acetate/ethyl ether to obtain colorless crystals (1.2 g), m.p. 78°–80° C.

Elemental analysis, Calcd. for $C_{15}H_{22}N_2O_2$: C, 68.67; H, 8.45; N, 10.68 Found: C, 68.40; H, 8.56; N, 10.47

EXAMPLE 5

4-(4-Pyrrolidinophenyloxy)piperidine fumarate

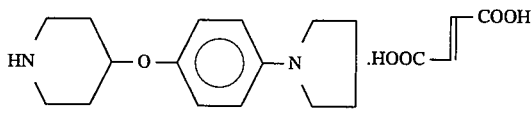

1-Acetyl-4-(4-pyrrolidinopheyloxy)piperidine (1.5 g) obtained in Example 1 was dissolved in a mixed solvent of ethanol (5 ml), water (5 ml) and conc. hydrochloric acid (5 ml), followed by heating with stirring at 100° C. for 15 hours. The solution was made basic with potassium carbonate and then extracted with ethyl acetate. The extract was dried over anhydrous magnesium sulfate and the solvent was distilled off. The residual oily compound (1.22 g) was dissolved in methanol (30 ml). After fumaric acid (0.52 g) was dissolved in the solution, the solvent was distilled off to leave a solid which was recrystallized from ethanol to obtain colorless crystals (1.4 g), m.p. 199°–201° C.

Elemental analysis, Calcd. for $C_{19}H_{26}N_2O_5$: C, 62.97; H, 7.23; N, 7.73 Found: C, 62.92; H, 7.21; N, 7.63

EXAMPLE 6

4-(4-Morpholinophenyloxy)piperidine fumarate

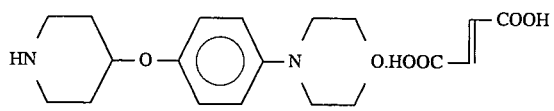

According to the same manner as that described in Example 5, colorless crystal (1.1 g), m.p. 208°–209° C., was obtained from 1-acetyl-4-(4-morpholinophenyloxy)piperidine (1.3 g) obtained in Example 2.

Elemental analysis, Calcd. for $C_{19}H_{26}N_2O_6$: C, 60.30; H, 6.93; N, 7.40 Found: C, 60.35; H, 7.09; N, 7.34

EXAMPLE 7

4-(4-Dimethylaminophenyloxy)piperidine fumarate

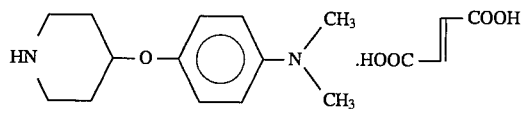

According to the same manner as that described in Example 5, colorless crystals (0.99 g), m.p. 191°–192° C was obtained from 1-acetyl-4-(4-dimethylaminophenyloxy)piperidine (1.0 g) obtained in Example 4.

Elemental analysis, Calcd. for $C_{17}H_{24}N_2O_5$: C, 60.70; H, 7.19; N, 8.33 Found: C, 60.77; H, 7.17; N, 8.31

EXAMPLE 8

4-(4-Isoindolynophenyloxy)piperidine dihydrochloride

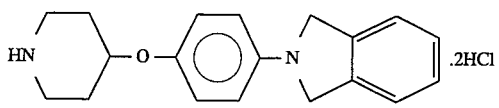

1-Acetyl-4-(4-isoindolynophenyloxy)piperidine (1.1 g) obtained in Example 3 was dissolved in a mixed solvent of ethanol (5 ml), water (5 ml) and conc. hydrochloric acid (5 ml), followed by heating with stirring at 100° C. for 15 hours. The solvent was distilled off and the solid thus obtained was rectrystallized from water/ethanol to obtain a colorless solid (0.9 g), m.p. 222°–226° C.

Elemental analysis, Calcd. for $C_{19}H_{24}C_{12}N_2O$: C, 62.13; H, 6.59; N, 7.63 Found: C, 61.92; H, 6.64; N, 7.35

EXAMPLE 9

1,3-Di(1-acetyl-4-piperidyloxy)-4-pyrrolidinobenzene

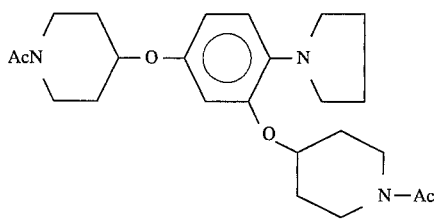

(1) 1-Acetyl-4-hydroxypiperidine (3.7 g) was dissolved in dimethylformamide (20 ml) and to the mixture was added sodium hydride (oily, 60 % 1.04 g) followed by , stirring at room temperature for 30 minutes. Then, 2,4-difluorobenzene (1.42 ml) was added dropwise. The mixture was worked up according to the same manner as that described in Example 1 and separated and purified by silica gel column chromatography (developing solvent: methanol/dichloromethane= 1/19 (v/v)) to obtain colorless crystals (3.6 g) of 1,3-di(1-acetyl-4-piperidyloxy)-4-nitrobenzene.

(2) 1,3-Di(1-acetyl-4-piperidyloxy)-4-nitrobenzene (3.7 g) was dissolved in a mixed solution of ethanol (30 ml) and conc. hydrochloric acid (1 ml) and then catalytic reduction was conducted according to the same manner as that described in Example 1, (2). After completion of the reaction, the catalyst was removed and then the solvent was distilled off to obtain 2,4-di(1-acetyl-4-piperidyloxy)aniline hydrochloride (3.9 g) as an amorphous solid. The amorphous solid (1.23 g) was dissolved in dimethylformamide (5 ml) and potassium carbonate (1.24 g) and 1,4-dibromobutane (0.36 ml) were added to the mixture, which was heated with stirring at 100° C. for one hour. After completion of the reaction, water (50 ml) was added to the reaction mixture, which was extracted with ethyl acetate. The extract was dried over anhydrous magnesium sulfate and then the solvent was distilled off. The residual oily compound was separated and purified by silica gel column chromatography (developing solvent: methanol/dichloroethane=1/19 (v/v)) to obtain an oily compound (0.9 g).

Elemental analysis, Calcd. for $C_{24}H_{35}N_3O_4$: C, 67.11; H, 8.21; N, 9.78 Found: C, 67.39; H, 8.15; N, 9.66

NMR (CDCl$_3$) δ; 1.5–2.1 (12H, m), 2.15 (6H, s), 3.1–3.3 (4H, m), 3.3–4.1 (8H, m), 4.2–4.6 (2H, m), 6.35–6.80 (2H, m), 8.03 (1H, s)

EXAMPLE 10

1,3-Di(4-piperidyloxy)-4-pyrrolidinobenzene 2 fumarate

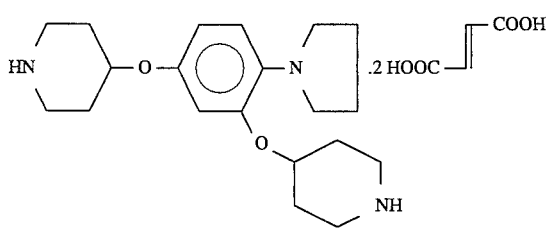

According to the same manner as that described in Example 5, a colorless amorphous solid (1.1 g) was obtained from 1,3-di(1-acetyl-4-piperidiloxy)-4-pyrrolidinobenzene (0.8 g).

NMR (D$_2$O+DMSO$_4$-d$_6$) δ: 1.5–2.3 (12H, m), 2.8–3.5 (12H, m), 4.3–4.8 (2H, m), 6.4–6.8 (3H, m), 6.60 (4H, s)

EXAMPLE 11

1-Methylaminocarbonyl-4-(4-pyrrolidinophenyloxy)-piperidine hydrochloride

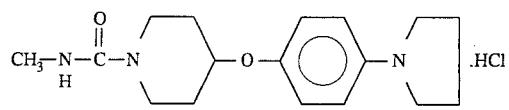

4-(4-Piperidinophenyloxy)piperidine (0.62 g) obtained during the synthesis of the compound of Example 5 was dissolved in ethyl acetate (10 ml) and to the mixture was added methylisocyanate (0.45 ml), followed by stirring at room temperature for one hour. The solvent was distilled off and the residual oily compound was separated and purified by silica gel column chromatography (developing solvent: ethyl acetate) and then converted into the hydrochloride to obtain a colorless amorphous solid (0.6 g).

Elemental analysis, Calcd. for $C_{17}H_{26}C_1N_3O_2$: C, 60.01; H, 7.71; N, 12.36 Found: C, 59.81; H, 7.43; N, 12.12

NMR (DMSO-d$_6$) δ: 1.2–1.7 (2H, m), 1.7–2.4 (6H, m), 2.63 (3H, s), 2.9–3.4 (2H, m), 3.4–3.9 (6H, m), 4.4–4.8 (1H, m), 6.95–7.20 (2H, m), 7.60–7.85 (2H, m)

EXAMPLE 12

4-[4-(4-Methylpentylamino)phenyloxy]piperidine fumarate

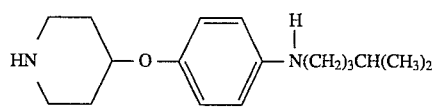

(1) 1-Acetyl-4-(4-nitrophenyloxy)piperidine (13.2 g) obtained in Example 1, (1) was dissolved in a mixed solvent of ethanol (40 ml) and conc. hydrochloric acid (40 ml), followed by heating with stirring at 100° C. for 15 hours. After the solvent was distilled off, water (100 ml) was added and to the mixture were added solid sodium bicarbonate (12.6 g) and di-tert-butyl-dicarbonate (16.4 g), followed by stirring at room temperature for 8 hours. The solution was extracted with ethyl acetate, the extract was dried over anhydrous magnesium sulfate and then the solvent was distilled off. The residual oily compound was separated and purified by silica gel column chromatography (developing solvent: dichloromethane) to obtain 1-tert-butyloxycarbonyl4-(4-nitrophenyloxy)piperidine (13 g).

NMR (CDCl$_3$) δ: 1.50 (9H, s), 1.5–2.2 (4H, m), 3.2–3.9 (4H, m), 4.50–4.80 (1H, m), 6.9–7.1 (2H, m), 8.15–8.35 (2H, m)

(2) 1-tert-Butyloxycarbonyl-4-(4-nitrophenyloxy)-piperidine (5.47 g) was dissolved in ethanol (100 ml). After conc. hydrochloric acid (2 ml) was added to the mixture, catalytic reduction was conducted according to the same manner as that described in Example 1, (2). After completion of the reaction, the catalyst was removed and then the solvent was distilled off to obtain an oily compound (5.6 g). To a solution of the oily compound (3.17 g) in dichloromethane (30 ml) were added triethylamine (4.2 ml) and isocaproic chloride (2.0 g), followed by stirring at room temperature for 30 minutes. To the reaction mixture was added water (50 ml) and the aqueous layer was made basic with solid potassim carbonate. Then, the organic layer was dried over anhydrous magnesium sulfate and the solvent was distilled off. The oily compound thus obtained was separated and purified by silica gel column chromatography (developing solvent: methanol/dichloromethane=1:99 (v/v)) to obtain an oily compound (1.9 g).

NMR (CDCl$_3$) δ: 0.93 (6H, d), 1.50 (9H, s), 1.5–2.1 (7H, m), 2.33 (2H, t), 3.1–3.5 (2H, m), 3.5–3.9 (2H, m), 4.3–4.6 (1H, m), 6.8–7.0 (2H, s), 7.30 (1H, broad), 7.35–7.55 (2H, m)

(3) 1-tert-Butyloxycarbonyl-4-[4-(4-methylvaleroylamino)phenyloxy]piperidine (1.90 g) was dissolved in trifluoroacetic acid (10 ml) which was allowed to stand at room temperature for 10 minutes. To this was added 6N solution of hydrogen chloride in dioxane (3 ml) and the solvent was distilled off. The solid thus obtained was recrystallized from ethanol/ethyl acetate to obtain colorless crystals (1.3 g), m.p. 258°–263° C.

(4) 4-[4-(4-methylvaleroylamino)phenyloxy]piperidine hydrochloride (1.3 g) was suspended in tetrahydrofuran (30 ml) and to this was added lithium aluminum hydride (1.44 g) by portions. After completion of addition, the suspension was heated with stirring at 60° C. for 30 minutes. To this were added water (2.4 ml) and 10% aqueous solution of sodium hydroxide (1.9 ml), followed by stirring at room temperature for 10 minutes. After the insoluble substance was filtered off, water (50 ml) and ethyl acetate (50 ml) were added. The organic layer was dried over anhydrous magnesium sulfate and the solvent was distilled off to obtain a colorless oily compound (1.1 g). The compound was dissolved in ethanol (20 ml) and to the mixture was added fumaric acid (0.42 g). The solvent was distilled off and the residual solid was recrystallized from ethanol/ethyl acetate to obtain colorless crystals (1.25 g), m.p. 138°–140° C.

Elemental analysis, Calcd. for $C_{21}H_{32}N_2O_5$: C, 64.26; H, 8.22; N, 7.14 Found: C, 64.14; H, 8.03; N, 7.18

EXAMPLE 13

1-tert-Butyloxycarbonyl-4-[(4-dimethylamino-phenyloxy)methyl]piperidine

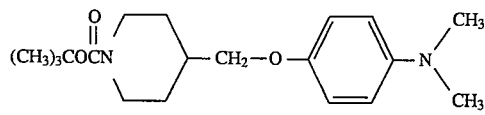

(1) 1-tert-Butyloxycarbonyl-4-piperidine acetic acid N-hydroxysuccinimide ester (15.0 g) was dissolved in dioxane (30 ml). The mixture was added dropwise to a suspension of sodium boron hydride (1.8 g) in a mixture of metanol and water (4:1) with ice cooling, followed by stirring with ice cooling for one hour. The reaction mixture was concentrated under reduced pressure, followed by addition of a water, saturation of salt and exraction with methylene chloride (100 ml×3). The combined extract was washed with saturated saline and dried over anhydrous magnesium sulfate and then the solvent was distilled off under reduced pressure. The residue thus obtained was purified by silica gel column chromatography (developing solvent: hexane/ethylacetate=1/1 (v/v)) to obtain 1-tert-butyloxycarbonyl-4-hydroxymethylpiperidine (3.2 g) as colorless crystals, m.p. 76°–78° C.

Elemental analysis, Calcd. for $C_{11}H_{21}NO_3$: C, 61.36; H, 9.83; N, 6.51 Found: C, 61.57; H, 10.11; N, 6.68

(2) 1-tert-Butyloxycarbonyl-4-hydroxymethylpiperidine (2.8 g) was dissolved in dimethylformamide (10 ml), followed by stirring for 30 minutes. To the mixture was added p-fluoronitrobenzene (2.1 g), followed by stirring at room temperature overnight. Aqueous saturated solution of sodium bicarbonate was added to the mixture which was extracted with methylene chloride (50 ml×3). The combined organic layer was washed with saturated saline and dried over sodium sulfate. The solvent was distilled off under reduced pressure and the residue thus obtained was purified by silica gel column chromatography (developing solvent: hexane/ethylacetate=5/1 (v/v)) to obtain 1-tert-butyloxycarbonyl-4-[(4-nitrophenyloxy)methyl]piperidine (1.9 g) as pale yellow crystals, m.p. 130°–131° C.

Elemental analysis, Calcd. for $C_{17}H_{24}N_2O_5$: C, 60.70; H, 7.19; N, 8.33 Found: C, 60.90; H, 7.20; N, 8.37

(3) 1-tert-Butyloxycarbonyl-4-[(4-nitrophenyloxy)methyl]piperidine (1.9 g) was dissolved in ethanol (40 ml) and to the mixture was added conc. hydrochloric acid (0.5 ml). By using 10% palladium/carbon as a catalyst, catalytic reduction was conducted at normal pressure and room temperature overnight. After completion of the reaction, the catalyst was removed by filtration and the filtrate was concentrated under reduced pressure. The concentrate was diluted with methylene chloride and washed with aqueous saturated solution of sodium bicarbonate. The organic layer was dried over sodium sulfate and concentrated under reduced pressure. The residue thus obtained was purified by silica gel column chromatography (developing solvent: hexane/ethyl acetate=1/1 (v/v)) to obtain 1-tert-butyloxycarbonyl-4-[(4-aminophenyloxy)methyl]piperidine (1.0 g) as white crystals, m.p. 100°–101° C.

Elemental analysis, Calcd. for $C_{17}H_{26}N_2O_3$: C, 66.64; H, 8.55; N, 9.14 Found: C, 66.42; H, 8.62; N, 9.07

(4) To 1-tert-Butyloxycarbonyl-4-[(4-aminophenyloxy)methyl]piperidine (0.9 g) was added trimethyl phosphate (0.7 ml) and the mixture was heated to 180° C. and stirred for 5 hours. 5% aqueous solution of sodium hydroxide (10 ml) was added to the reaction mixture which was heated under reflux for one hour, diluted with water and extracted with ethyl acetate (50 ml×3). The combined organic layer was dried over sodium sulfate and concentrated under reduced pressure. The residue thus obtained was purified by silica gel column chromatography (developing solvent: hexane/ethyl acetate=5/1 (v/v)) to obtain 1-tert-butyloxycarbonyl-4-[(4-dimethylphenyloxy)methYl]PiPeridine (0.13 g) as pale yellow crystals, m.p. 91°–93° C.

Elemental analysis, Calcd. for $C_{19}H_{30}N_2O_3$: C, 68.23; H, 9.04; N, 8.38 Found: C, 68.13; H, 8.89; N, 8.51

EXAMPLE 14

4-[(4-Dimethylaminophenyloxy)methyl]piperidine ½ fumarate

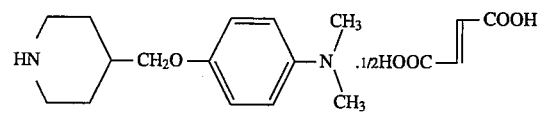

To 1-tert-Butyloxycarbonyl-4-[(4-dimethylaminophenyloxy)methyl]piperidine (0.1 g) obtained in Example 13 was added trifluoroacetic acid (0.5 ml) followed by stirring at room temperature for 10 minutes. The reaction mixture was concentrated under reduced pressure, and the concentrate was diluted with methylene chloride (100 ml) and washed with aqueous saturated solution of sodium bicarbonate. The organic layer was separated, dried over sodium sulfate and concentrated under reduced pressure. The residue was treated with fumaric acid and the resulting fumarate was recrystallized from methanol to obtain 4-[(4-dimethylaminophenyloxy)methyl]piperidine ½ fumarate (0.1 g) as pale yellow crystals, m.p. 210°–213° C.

Elemental analysis, Calcd. for $C_{16}H_{24}N_2O_3$: C, 65.72; H, 8.27; N, 9.58 Found: C, 65.43; H, 8.38; N, 9.57

EXAMPLE 15

1-tert-Butyloxycarbonyl-4-[(4-pyrrolidinophenyloxy)methyl]piperidine

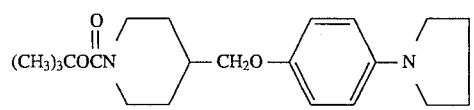

To 1-tert-butyloxycarbonyl-4-[(4-aminophenyloxy)methyl]piperidine (0.75 g) obtained in Example 13 were added dimethylformamide (10 ml), potassium carbonate (1.4 g) and dibromobutane (0.54 g) and the mixture was heated to 70° C. and stirred overnight. To the reaction solution was added water which was extracted with ethyl acetate (50 ml×3). The combined extract was dried over sodium sulfate and concentrated under reduced pressure. The residue thus obtained was purified by silica gel column chromatography (developing solvent: hexane/ethyl acetate= 5/1 (v/v)) to obtain 1-tert-butyloxycarbonyl-4-[(4-pyrrolidinophenyloxy)methyl]piperidine (0.55 g) as colorless crystals, m.p. 141°–145° C.

Elemental analysis, Calcd. for $C_{21}H_{32}N_2O_3$: C, 69.96; H, 8.95; N, 7.77 Found: C, 69.71; H, 8.88; N, 7.85

EXAMPLE 16

4-[(4-Pyrrolidinophenyloxy)methyl]piperidine

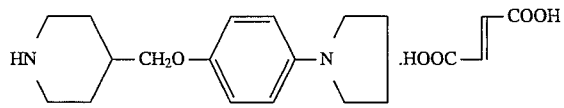

To 1-tert-butyloxycarbonyl-4-[(4-pyrrolidinophenyloxy)methyl]piperidine (0.55 g) obtained in Example 15 was added trifluoroacetic acid (2 ml), followed by stirring at room temperature for 10 minutes. The mixture was worked up according to the same manner as that described in Example 14 to obtain a fumarate and the fumarate was recrystallized from water/ethanol (½) to obtain 4-[(4-pyrrolidinophenyloxy)methyl]piperidine fumarate (0.5 g) as colorless crystals, m.p. 200°–205° C.

Elemental analysis, Calcd. for $C_{20}H_{28}N_2O_5$: C, 63.81; H, 7.50; N, 7.44 Found: C, 63.57; H, 7.53; N, 7.44

EXAMPLE 17

N-(4-ethylaminophenyl)piperidine dihydrochloride

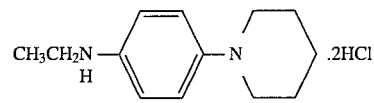

(1) A solution of p-fluoronitrobenzene (31.8 ml) in dimethylformamide (200 ml) was ice-cooled and to this was added piperidine (60 ml) dropwise, followed by stirring with ice cooling for 2 hours. After the solvent was distilled off, the residual oily product was dissolved in ethyl acetate ester (200 ml), followed by washing in turn with aqueous saturated solution of sodium bicarbonate and water. Then, the solution was dried over anhydrous magnesium sulfate. After the solvent was distilled off, the residue was recrystallized from n-hexane to obtain N-(4-nitrophenyl)piperidine as yellow crystals (52.8 g).

(2) To a solution of N-(4-nitrophenyl)piperidine (12 g) in methanol (50 ml) was added conc. hydrochloric acid (12 ml) and, by using 10% palladium/carbon as a catalyst, catalytic reduction was conducted at normal temperature and normal pressure. After completion of the reaction, the catalyst was removed and the solvent was distilled off. To the residue was added ethyl ether which was filtered off to obtain N-(4-aminophenyl)piperidine dihydrochloride (13.7 g) as a colorless solid.

(3) A solution of N-(4-aminophenyl)piperidine dihydrochloride (2.49 g) and triethylamine (5.6 g) in dichloroform (30 ml) was ice-cooled and to this was added dropwise acetyl chloride (1.42 ml). After stirred at room temperature for 30 minutes, water (10 ml) was added to the mixture and the organic layer was dried over anhydrous magnesium sulfate. The solvent was distilled off and then the residue was recrystallized from ethyl ether to obtain N(4-acetylaminophenyl)piperidine (2 g) as colorless crystals, m.p. 150°–152° C.

Elemental analysis, Calcd. for $C_{13}H_{18}N_2O$: C, 71.53; H, 8.31; N, 12.83 Found: C, 71.51; H, 8.31; N, 12.80

(4) N-(4-Acetylaminophenyl)piperidine (1.96 g) was suspended in tetrahydrofuran (30 ml) and to the mixture was added lithium aluminum hydride (0.54 g), followed by stirring at 60° C. for 30 minutes. To the mixture was added water (0.9 ml) and 10% aqueous solution of sodium hydroxide (0.72 ml) which was stirred at room temperature for 30 minutes. Then, the precipitate was filtered off and 6N hydrogen chloride in dioxane was added to the mother liquor to form a white precipitate. The precipitate was filtered off and recrystallized from ethanol to obtain colorless crystals (2.10 g), m.p. 182°–197° C.

Elemental analysis, Calcd. for $C_{13}H_{20}N_2.2HCl$: C, 56.33; H, 8.00; N, 10.11 Found: C, 56.60; H, 7.95; N, 9.94

EXAMPLE 18

According to the same maner as that described in Example 17, the compounds shown in Table 1 were obtained.

TABLE 1

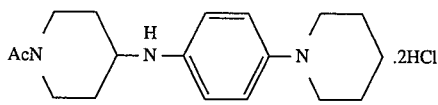

| Compound No. | $R_1'$ | Melting point (°C.) | Molecular formula | Elemental analysis Calcd. (Found) C | H | N |
|---|---|---|---|---|---|---|
| 1 | $(CH_3)_2CH(CH_2)_3$ | 161–169 | $C_{17}H_{30}Cl_2N_2$ | 61.25 (61.53) | 9.07 (9.12) | 8.40 (8.21) |
| 2 | $CH_3(CH_2)_3$ | 168–171 | $C_{15}H_{26}Cl_2N_2$ | 59.01 (58.92) | 8.58 (8.64) | 9.18 (9.08) |
| 3 | $\phi CH_2$ | 165–170 | $C_{18}H_{28}Cl_2N_2$ | 63.71 (63.66) | 7.13 (7.27) | 8.26 (8.32) |
| 4 | $CH_3(CH_2)_5$ | 160–175 | $C_{17}H_{30}Cl_2N_2$ | 61.25 (61.10) | 9.07 (9.25) | 8.40 (8.35) |
| 5 | $CH_3(CH_2)_9$ | 121–135 | $C_{21}H_{38}Cl_2N_2$ | 64.76 (64.54) | 9.83 (9.69) | 7.19 (7.06) |
| 6 | $CH_3(CH_2)_{15}$ | 145–155 | $C_{27}H_{50}Cl_2N_2$ | 68.47 (68.63) | 10.64 (10.35) | 5.91 (5.84) |

EXAMPLE 19

1-acetyl-4-[4-(piperidin-1-yl)phenylamino]piperidine dihydrochloride

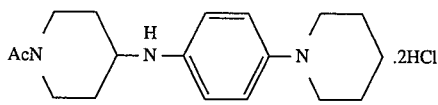

To a solution of N-(4-aminophenyl)piperidine dihydrochloride obtained in Example 17 and 1-acetyl-4-piperidone (0.70 g) in methanol (10 ml) was added sodium cyano borohydride (0.63 g), followed by stirring at room temperature for 5 hours. To the mixture was added ethyl acetate ester (20 ml) and water (30 ml). After the organic layer was dried over anhydrous sodium sulfate, to the solution was added 6N solution of hydrogen chloride in dioxane (2 ml) and the solvent was distilled off. The residue was recrystallized from ethanol to obtain colorless crystals, m.p. 187°–193° C.

Elemental analysis, Calcd. for $C_{18}H_{29}Cl_2N_3O$: C, 57.75; H, 7.81; N, 11.22 Found: C, 57.79; H, 7.61; N, 11.02

EXAMPLE 20

4-[4-(piperidin-1-yl)phenylamino]piperidine trihydrochloride

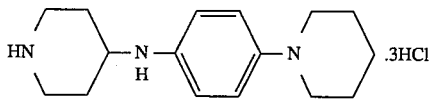

A solution of 1-acetyl-4-[4-(piperidin-1-yl)phenylamino] piperidine dihydrochloride (0.70 g) in conc. hydrochloric acid (5 ml) was heated with stirring at 100° C. for 15 hours. After the solvent was distilled off, the residue was recrystallized from ethanol to obtain colorless crystals (0.5 g), m.p. 185°–189° C.

Elemental analysis, Calcd. for $C_{16}H_{28}C_{13}N_3$: C, 52.11; H, 7.65; N, 11.39 Found: C, 52.23; H, 7.63; N, 11.14

EXAMPLE 21

1-Acetyl-4-[3-(piperidin-1-yl)phenylamino]-piperidine dihydrochloride

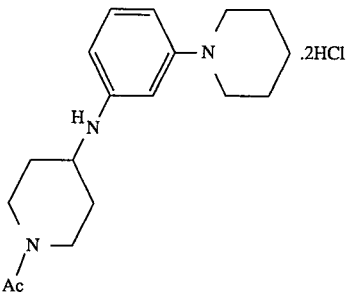

(1) A mixture of m-fluoronitrobenzene (9 g) and piperidine (40 ml) was heated with stirring at 100° C. for 15 hours and to the mixture were added ethyl acetate ester (100 ml) and aqueous saturated solution of potassium carbonate (100 ml). The organic layer was washed with water and dried over anhydrous sodium sulfate. The solvent was distilled off to obtain N-(3-nitrophenyl)piperidine (13.5 g) as a yellow oily compound.

(2) To a solution of N-(3-nitrophenyl)piperidine (12 g) in methanol (50 ml) was added conc. hydrochloric acid (12 ml) and, by using 10% palladium/carbon as a catalyst, catalytic reduction was conducted at normal temperature under normal pressure. After completion of the reaction, the catalyst was removed and the solvent was distilled off. Ethyl ether was added to the residue and the mixture was filtered off to obtain N-(3-aminophenyl)piperidine dihydrochloride (13.2 g) as a colorless solid.

(3) To a solution of N-(3-aminophenyl)piperidine dihydrochloride (3.73 g) and 1-acetyl-4-piperidone (2.1 g) in methanol (30 ml) was added sodium cyano borohydride (1.9 g), followed by stirring at room temperature for 5 hours. To the mixture were added ethyl acetate ester (20 ml) and water (30 ml), the organic layer was dried over anhydrous sodium sulfate and then the solvent was distilled off. The residual oily compound was separated and purified by silica gel column chromatography (developing solvent: ethyl acetate ester). The oily compound was dissolved in dioxane (10 ml)

and to the mixture was added 6N solution of hydrogen chloride in dioxane (2 ml). Then, the solvent was removed to obtain a colorless amorphous solid (3.7 g).

NMR (D$_2$O) δ: 1.2–2.3 (10H, m), 2.03 (3H, s), 2.5–2.9 (1H, m), 3.0–3.5 (1H, m), 3.5–3.8 (5H, m), 3.8–4.2 (2H, m), 7.1–7.8 (4H, m)

EXAMPLE 22

4-[3-(Piperidin-1-yl)phenylamino]piperidine trihydrochloride

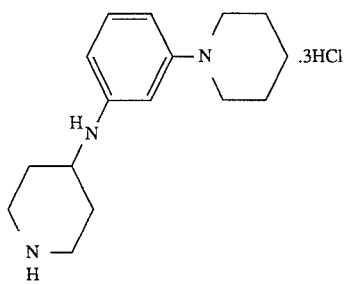

According to the same manner as that described in Example 20, colorless crystals (0.84 g) having m.p. of 176°–79° C. was obtained from 1-acetyl-4-[3-(piperidin-1-yl)phenylamino]piperidine trihydrochloride (1.0 g).

Elemental analysis, Calcd. for C$_{16}$H$_{28}$Cl$_3$N$_3$: C, 52.11; H, 7.65; N, 1.39 Found: C, 52.02; H, 7.69; N, 11.01

EXAMPLE 23

4-[4-(4-Hexadecanylamino)-2-methylphenyloxy]-piperidine 2 fumarate

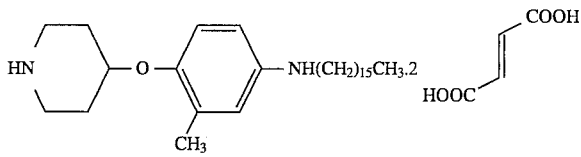

(1) 1-Acetyl-4-hydroxypiperidine (9.2 g) was dissolved in dimethylformamide (20 ml) and to the solution was added sodium hydride (oily, 60%, 2.6 g). The mixture was stirred at room temperature for 30 minutes, followed by adding dropwise 2-fluoro-5-nitrotoluene (10 g). The mixture was stirred at room temperature for 10 minutes. To the reaction mixture was added water (50 ml) which was extracted with methylene chloride (50 ml×3). The extract was dried over anhydrous sodium sulfate and the solvent was distilled off. The residue was purified by silica gel chromatography (developing solvent: methylene chloride/methanol=20/1 (v/v)) to obtain 1-acetyl-4-(4-nitro-2-methylphenyloxy)piperidine (12.6 g) as yellow crystals, m.p. 139°–141° C.

(2) To 1-acetyl-4-(4-nitro-2-methylphenyloxy)piperidine (11.8 g) were added conc. hydrochloric acid (15 ml), ethanol (15 ml) and water (15 ml) and the mixture was heated under reflux overnight. The reaction mixture was concentrated under reduced pressure, the residue thus obtained was washed with ethyl ether and crystals were filtered off to obtain 4-(4-nitro-2-methylphenyloxy)piperidine hydrochloride (8.3 g) as white crystals, m.p. 204°–226° C.

(3) To a suspension of 4-(4-nitro-2-methylphenyloxy)piperidine hydrochloride (7.5 g) in methylene chloride (30 ml) were added dropwise triethylamine (5.56 g) and di-tert-butyl dicarbonate (7.2 g) and the mixture was stirred with ice cooling for 10 minutes. To the reaction mixture was added water, which was extracted with methylene chloride (50 ml×3). The combined extract was dried over anhydrous sodium sulfate and concentrated under reduced pressure. The resulting residue was washed with n-hexane to obtain 1-tert-butyloxycarbonyl-4-(4-nitro-2methylphenyloxy)piperidine (9.7 g) as yellow crystals, m.p. 82°–83° C.

(4) To a solution of 1-tert-butyloxycarbonyl-4-(4-nitro-2-methylphenyloxy)piperidine (9.0 g) in ethanol (100 ml) was added conc. hydrochrolic acid (2.3 ml) and, by using 10% palladium/carbon (containing 48% of water, 1 g) as a catalyst, catalytic reduction was conducted under normal pressure for 1.5 hours. The catalyst was removed by filtration and the filtrate was concentrated under reduced pressure to obtain 1-tert-butyloxycarbonyl-4-(4-amino-2-methylphenyloxy)piperidine (8.7 g) as a light brown amorphous material.

(5) To a solution of 1-tert-butyloxycarbonyl-4-(4-amino-2-methylphenyloxy)piperidine (1.5 g) in methylene chloride (30 ml) were added triethylamine (1.3 g) and palmitoyl chloride (1.2 g) with ice-cooling and the mixture was stirred at room temperature for 1 hour. Aqueous saturated solution of sodium bicarbonate was added to the reaction mixture and the organic layer was separated. The aqueous layer was further extracted with methyene chloride (50 ml×2) and the combined orgnaic layer was dried over sodium sulfate and concentrated under reduced pressure. To the solidified residue was added trifluoroacetic acid (5 ml) and the mixture was stirred at room temperature for 30 minutes. After concentration of the reaction mixture under reduced pressure, the resulting residue was dissolved in ethanol and conc. hydrochloric acid (0.37 ml) was added. The resulting solution was concentrated under reduced pressure and the residue was washed with hexane to obtain 4-(4-palmitoylamino-2-methylphenyloxy)piperidine hydrochloride (1.8 g) as white crystals, m.p. 125°–137° C.

Elemental analysis, Calcd. for C$_{28}$H$_{49}$N$_2$O$_2$Cl: C, 69.89; H, 10.27; N, 5.82 Found: C, 70.01; H, 10.22; N, 5.93

(6) According to the same manner as that described in Example 12, (4), coloress crystals (1.3 g) having m.p. of −116°–160° C. were obtained from 4-(4-palmitoylamino-2-methylphenyloxy)piperidine hydrochloride (1.5 g).

Elemental analysis, Calcd. for C$_{36}$H$_{58}$N$_2$O$_9$: C, 65.23; H, 8.82; N, 4.23 Found: C, 65.62; H, 8.99; N, 4.60

EXAMPLES 24–27

According to the same manner as that described in Example 23, the compounds shown in Table 2 were obtained.

TABLE 2

| | | | m.p. | Elemental Analysis | | |
|---|---|---|---|---|---|---|
| Ex. No. | R | Salt | (°C.) | Exp. formula | Calcd. | Found |
| 24 | —(CH$_2$)$_{15}$CH$_3$ | 2 fumarate | 116–160 | C$_{36}$H$_{58}$N$_2$O$_9$ | C 65.23<br>H 8.82<br>N 4.23 | C 65.62<br>H 8.99<br>N 4.60 |
| 25 | —(CH$_2$)$_9$CH$_3$ | fumarate | amorphous* | C$_{26}$H$_{42}$N$_2$O$_5$ | C 67.50<br>H 9.15<br>N 6.06 | C 67.72<br>H 9.13<br>N 6.24 |
| 26 | —(CH$_2$)$_5$CH$_3$ | fumarate | 125–134 | C$_{22}$H$_{34}$N$_2$O$_5$ | C 65.00<br>H 8.43<br>N 6.89 | C 65.21<br>H 8.53<br>N 6.97 |
| 27 | —(CH$_2$)$_3$CH(CH$_3$)$_2$ | fumarate | amorphous** | C$_{22}$H$_{34}$N$_2$O$_5$ | C 65.00<br>H 8.43<br>N 6.89 | C 64.81<br>H 8.52<br>N 6.77 |

*spectrum of Example 25
NMR(D$_2$O)δ: 0.73(3H, br), 1.10(14H, br), 1.55(2H, br), 1.91(4H, br), 2.04(3H, br), 3.04–3.27(6H, m), 4.42(1H, br), 6.52(2H, br), 6.78–6.82(1H, m), 6.88–7.02(2H, m).
**spectrum of Example 27
NMR(D$_2$O)δ: 0.82(6H, d, J=6.6Hz), 1.15–1.26(2H, m), 1.41–1.72(3H, m), 2.04–2.21(4H, m), 2.26(3H, s), 3.18–3.47(6H, m), 4.67(1H, m), 6.53(2H, s), 7.09(1H, d, J=8.4Hz), 7.20–7.26(2H, m).

EXAMPLE 28

4-(4-Decanylamino-3-methylphenyloxy)piperidine fumarate

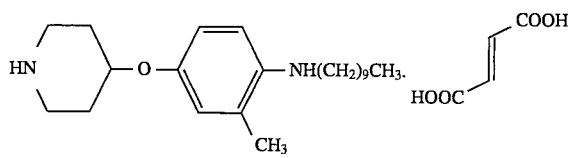

(1) 1-Acetyl-4-hydroxypiperidine (9.2 g) was dissolved in dimethylformamide (20 ml) and to the solution was added sodium hydride (oily, 60%, 2.6 g). The mixture was stirred at room temperature for 30 minutes and 5-fluoro-2-nitortoluene (10 g) was added dropwise thereto. The mixture was stirred at room temperature for 10 minutes. Water (50 ml) was added to the reaction mixture which was extracted with methylene chloride (50 ml×3). The extract was dried over anhydrous sodium sulfate and the solvent was distilled off. To the resulting residue were added conc. hydrochloric acid (15 ml), ethanol (15 ml) and water (15 ml) and the mixture was heated at reflux overnight. The reaction mixture was concentrated under reduced pressure and the resulting residue was washed with ethyl ether and crystals were filtered off to obtain 4-(4-nitro-3-methylphenyloxy)piperidine hydrochloride (2.8 g) as yellow crystals, m.p. 233°–236° C.

(2) To a suspension of 4-(4-nitro-3-methylphenyloxy)piperidine hydrochloride (2,8 g) in methylene chloride (20 ml) were added dropwise triethylamine (2.1 g) and di-tert-butyl dicarbonate (2.7 g) and the mixture was stirred with ice-cooling for 20 minutes. Water was added to the reaction mixture, which was extracted with methylene chloride (50 ml×3). The combined extract was dried over anhydrous sodium sulfate and concentrated under reduced pressure. The resulting residue was washed with ethyl ether to obtain 1-tert-butyloxycarbonyl-4-(4-nitro-3-methylphenyloxy)piperidine (3.6 g) as yellow crystals, m.p. 104°–106° C.

(3) To a solution of 1-tert-butyloxycarbonyl-4-(4-nitro-3-methylphenyloxy)piperidine (3.6 g) in ethanol (30 ml) was added conc. hydrochloric acid (0.9 ml). By using 10% palladium/carbon (containing 48% water, 0.3 g) as a catalyst, catalytic reduction was conducted under reduced pressure for 1.5 hours. The catalyst was removed by filtration and the filtrate was concentrated under reduced pressure to obtain 1-tert-butyloxycarbonyl-4-(4-amino-3methylphenyloxy)piperidine hydrochloride (1.7 g) as light brown crystals, m.p. 160°–180° C.

(4) To a solution of 1-tert-butyloxycarbonyl-4-(4-amino-3-methylphenyloxy)piperidine hydrochloride (0.7 g) in methylene chloride (10 ml) were added triethylamine (0.62 g) and decanoyl chloride (0.39 g) with ice-cooling and the mixture was stirred at room temperature for 1 hour. Aqueous saturated solution of sodium dicarbonate was added to the reaction mixture and the organic layer was separated. The aqueous layer was further extracted with methylene chloride (50 ml×2) and the combined organic layer was dried over sodium sulfate and concentrated under reduced pressure. To the solidified residue was added trifluoroacetic acid (5 ml) and the mixture was stirred at room temperature for 30 minutes. The reaction mixture was concentrated under reduced pressure, the resulting residue was dissolved in ethanol and conc. hydrochloric acid (0.20 ml) was added thereto. The resulting solution was concentrated under reduced pressure and the residue was washed with hexane to obtain 4-(4-decanoylamino-3-methylphenyloxy)piperidine hydrochloride (0.93 g) as white crystals, m.p. 177°–195° C.

Elemental analysis, Calcd. for $C_{22}H_{37}N_2O_2Cl$: C, 66.56; H, 9.39; N, 7.06 Found: C, 66.39: H, 9.36; N, 6.91

(5) According to the same manner as that described in Example 12, (4), colorless crystals (0.43 g) having m.p. of 110°–129° C. were obtained from 4-(4-decanylamino-3-methylphenyloxy)piperidine hydrochloride (0.8 g).

Elemental analysis, Calcd. for $C_{26}H_{42}N_2O_5$: C, 67.50; H, 9.15; N, 6.06 Found: C, 67.66; H, 9.10; N, 6.17

EXAMPLE 29

4-4-(Hexanylamino-3-methylphenyloxy)piperidine fumarate

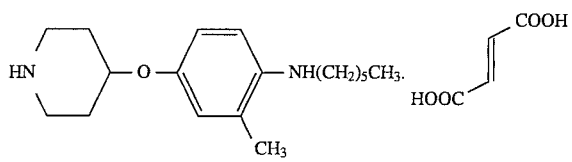

According to the same manner as that described in Example 28, colorless crystals having m.p. of 131°–140° C. were obtained.

Elemental analysis, Calcd. for $C_{22}H_{34}N_2O_5$: C, 65.00; H, 8.43; N, 6.85 Found: C, 65.18; H, 8.54; N, 7.06

EXAMPLE 30

1-Acetyl-4-(4-pentylaminophenyloxy)piperidine

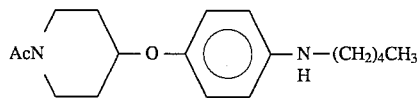

1-Acetyl-4-(4-aminophenyloxy)piperidine hydrochloride (2.5 g) obatined in Example 1, (2) was dissolved in methanol (20 ml) and to the solution were added sodium cyano borohydride (1.2 g) and pentylaldehyde (0.8 g) at room temperature. The mixture was stirred at room temperature for 1 hour. To the mixture was added aqueous saturated solution of sodium bicarbonate (50 ml) and the mixture was extracted with methylene chloride (50 ml×3). The combined extract was dried over anhydrous sodium sulfate and concentrated under reduced pressure. The resulting residue was purified by silica gel column chromatography (delveoping solvent: ethyl acetate/hexane=3/1 (v/v)) to obtain 1-acetyl-4-(4-pentylaminophenyloxy)piperidine (2.1 g) as white crystals, m.p. 69°–71° C.

Elemental analysis, Calcd. for $C_{18}H_{28}N_2O_2$: C, 71.02; H, 9.27; N, 9.20 Found: C, 70.92; H, 9.37; N, 9.09

EXAMPLES 31–44

According to the same manner as that described in Example 30, the compounds shown in Table 3 were obtained.

TABLE 3

| Ex. No. | R | Data |
|---|---|---|
| 31 | —(CH$_2$)$_2$CH$_3$ | oil.NMR(CDCl$_3$)δ: 0.99(3H, t, J=7.4Hz), 1.63(2H, q, J=7.4Hz), 1.73–1.96(4H, m), 2.11(3H, s), 3.04(2H, t, J=7.0Hz), 3.36(1H, ddd, J=4.0, 6.6, 13.8Hz), 3.50–3.85(3H, m), 4.28–4.38(1H, m), 6.56(2H, d, J=9.0Hz), 6.80(2H, d, J=9.0Hz). |
| 32 | —(CH$_2$)$_5$CH$_3$ | mp 51–53° C. Elemental analysis for C$_{19}$H$_{30}$N$_2$O$_2$ Calcd.: C 71.66; H 9.50; N 8.80 Found: C 71.61; H 9.71; N 8.56 |
| 33 | —(CH$_2$)$_6$CH$_3$ | mp 54–55° C. Elemental analysis for C$_{20}$H$_{32}$N$_2$O$_2$ Calcd.: C 72.25; H 9.70; N 8.43 |

TABLE 3-continued

AcN—[piperidine]—O—[phenyl]—N(H)—R

| Ex. No. | R | Data |
|---|---|---|
| 34 | —(CH$_2$)$_7$CH$_3$ | Found: C 72.54; H 9.77; N 8.35<br>mp 65–67° C. Elemental analysis for C$_{21}$H$_{34}$N$_2$O$_2$<br>Calcd.: C 72.79; H 9.89; N 8.08 |
| 35 | —(CH$_2$)$_8$CH$_3$ | Found: C 72.88; H 9.70; N 8.37<br>mp 64–65° C. Elemental analysis for C$_{22}$H$_{36}$N$_2$O$_2$<br>Calcd.: C 73.29; H 10.06; N 7.77<br>Found: C 73.53; H 10.10; N 7.66 |
| 36 | —CH$_2$—(2,3,4-trimethoxyphenyl) | oil.NMR(CDCl$_3$)δ: 1.70–1.97(4H, m), 2.11(3H, s), 3.35(1H, ddd, J=4.0, 6.6, 13.6Hz), 3.48–3.79(3H, m), 3.85(9H, s), 4.22(2H, s), 4.30–4.40(1H, m), 6.62(2H, s), 6.62(2H, d, J=9.0Hz), 6.81(2H, d, J=9.0Hz). |
| 37 | —CH$_2$—Ph | oil.NMR(CDCl$_3$)δ: 1.68–1.95(4H, m), 2.10(3H, s), 3.35(1H, ddd, J=4.0, 6.6, 13.4Hz), 3.50–3.85(3H, m), 4.28(2H, s), 4.28–4.38 (1H, m), 6.59(2H, d, J=9.0Hz), 6.79(2H, d, J=9.0Hz), 7.20–7.36 (5H, m). |
| 38 | —CH$_2$CH=CH—Ph | mp 114–116° C. Elemental analysis for C$_{22}$H$_{26}$N$_2$O$_2$<br>Calcd.: C 75.39; H 7.48; N 8.00<br>Found: C 75.53; H 7.24; N 7.89 |
| 39 | cyclohexyl | mp 101–103° C. Elemental analysis for C$_{19}$H$_{28}$N$_2$O$_2$<br>Calcd.: C 72.11; H 8.92; N 8.86<br>Found: C 72.38; H 8.79; N 8.77 |
| 40 | cyclopentyl | mp 114–116° C. Elemental analysis for C$_{18}$H$_{26}$N$_2$O$_2$<br>Calcd.: C 71.49; H 8.67; N 9.27<br>Found: C 71.27; H 8.78; N 9.33 |
| 41 | CH(CH$_3$)(CH$_2$)$_8$CH$_3$ | oil.NMR(CDCl$_3$)δ: 0.85–0.91(3H, m), 1.15(3H, d, J=6.2Hz), 1.26–1.57 (16H, m), 1.72–1.94(4H, m), 2.11(3H, s), 3.28–3.41(2H, m), 3.50–3.86(3H, m), 4.27–4.37(1H, m), 6.25(2H, d, J=9.0Hz), 6.78 (2H, d, J=9.0Hz). |
| 42 | CH(Ph)(CH$_2$)$_8$CH$_3$ | oil.NMR(CDCl$_3$)δ: 0.84–0.90(3H, m), 1.24–1.29(14H, m), 1.63–1.90 (6H, m), 2.09(3H, s), 3.28(1H, ddd, J=4.0, 6.8, 13.6Hz), 3.46–3.82 (3H, m), 4.17–4.31(2H, m), 6.44(2H, d, J=9.0Hz), 6.68(2H, d, J=9.0Hz), 7.18–7.35(5H, m). |
| 43 | —(CH$_2$)$_9$OAc | oil.NMR(CDCl$_3$)δ: 1.32(10H, brm), 1.57–1.65(4H, m), 1.73–1.94 (4H, m), 2.05, 2.11(each 3H, each s), 3.06(2H, t, J=7.0Hz), 3.35 (1H, ddd, J=4.2, 6.8, 13.6Hz), 3.50–3.86(3H, m), 4.06(2H, t, J=6.8 Hz), 4.28–4.38(1H, m), 6.56(2H, d, J=9.0Hz), 6.80(2H, d, J=9.0Hz). |
| 44 | —(CH$_2$)$_9$COOMe | mp 76–79° C. Elemental analysis for C$_{24}$H$_{38}$N$_2$O$_4$<br>Calcd.: C 68.86; H 9.15; N 6.69<br>Found: C 68.68; H 9.33; N 6.81 |

EXAMPLE 45

1-Acetyl-4-[4-(1-methylpentyl)amino-2-methyl]-piperidine

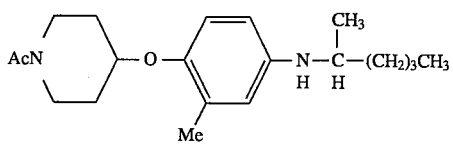

(1) To a solution of 1-Acetyl-4-(4-nitro-2methylphenyoxy)piperidine (4.5 g) obtained in Example 23, (1) in ethanol (70 ml) was added conc. hydrochloric acid (1.4 ml) and, by using 10% palladium/carbon (containing 48% water, 0.5 g) as a catalyst, catalytic reduction was conducted under normal pressure for 2 hours. The catalyst was removed by filtration and the filtrate was concentrated under reduced pressure to obtain 1-acetyl-4-(4-amino-2methylphenyloxy)piperidine hydrochloride (5.1 g) as a light brown amorphous material.

NMR (D$_2$O) δ: 1.72–2.01 (4H, m), 2.09 (3H, s), 2.21 (3H, s), 3.40–3.53 (2H, m), 3.64–3.75 (2H, m), 7.07–7.19 (3H, m)

(2) According to the same manner as that described in Example 30, 1-acetyl-4-[4-(1-methylpentyl)amino-2methylphenyloxy]piperidine (0.78 g) as a light brown oil from 1-acetyl-4-(4-amino-2-methylphenyloxy)piperidine hydrochloride (1.0 g).

NMR (CDCl₃) δ: 0.87–0.94 (3H, m), 1.14 (3H, d, J=6.4 Hz), 1.30–1.58 (6H, m), 1.75–1.93 (4H, m), 2.11 (3H, s), 2.18 (3H, s), 3.28–3.42 (2H, m), 3.51–3.85 (3H, m), 4.25–4.35 (1H, m), 6.35 (1H, dd, J=2.8, 8.6 Hz), 6.43 (1H, d, J=2.8 Hz), 6.69 (1H, d, J=8.6 Hz)

EXAMPLES 46–48

According to the same manner as that described in Example 45, the compounds shown in Table 4 were obtained.

TABLE 4

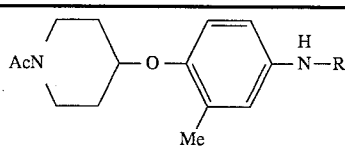

| Ex. No. | R | Data |
|---|---|---|
| 46 | CH₂CH₃ / (CH₂)₃CH₃ | oil.NMR(CDCl₃)δ: 0.85–0.95(6H, m), 1.31–1.57(8H, m), 1.79–1.90 (4H, m), 2.11(3H, s), 2.18(3H, s), 3.15(1H, quintet, J=5.8 Hz), 3.35(2H, ddd, J=4.4, 7.0, 12.8Hz), 3.52–3.85(3H, m), 4.24–4.34 (1H, m), 6.35(1H, dd, J=2.6, 8.4Hz), 6.42(1H, d, J=2.6Hz), 6.68(1H, d, J=8.4Hz). |
| 47 | (CH₂)₃CH₃ / (CH₂)₃CH₃ | oil.NMR(CDCl₃)δ: 0.85–0.92(6H, m), 1.26–1.50(12H, m), 1.76–1.92 (4H, m), 2.11(3H, s), 2.17(3H, s), 3.22(1H, quintet, J=5.8 Hz), 3.36(2H, ddd, J=4.4, 6.2, 13.8Hz), 3.52–3.83(3H, m), 4.24–4.34 (1H, m), 6.34(1H, dd, J=3.2, 8.4Hz), 6.41(1H, d, J=3.2Hz), 6.68(1H, d, J=8.4Hz). |
| 48 | Ph / (CH₂)₃CH₃ | oil.NMR(CDCl₃)δ: 0.84–0.91(3H, m), 1.26–1.38(4H, m), 1.70–1.83 (6H, m), 2.09, 2.11(each 3H, each s), 3.31(1H, ddd, J=4.0, 7.0, 13.4Hz), 3.49–3.80(3H, m), 4.16–4.29(2H, m), 6.23(1H, dd, J=3.0, 8.6Hz), 6.39(1H, d, J=3.0Hz), 6.58(1H, d, J=8.6Hz), 7.17–7.35 (5H, m). |

EXAMPLES 49–66

According to the same manner as that described in Example 5, the compounds shown in Tables 5 and 6 were obtained from the compounds of Examples 30, 31 and 33 to 48.

TABLE 5

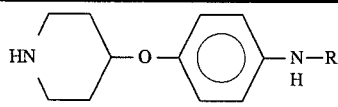

| | | m.p. | | Elemental analysis | |
|---|---|---|---|---|---|
| Ex. No. | R.Salt | (°C.) | Exp. formula | Calcd. | Found |
| 49 | —(CH₂)₂CH₃.fumarate | 157–162 | C₁₈H₂₆N₂O₅ | C 61.70<br>H 7.48<br>N 7.99 | C 61.93<br>H 7.40<br>N 7.87 |
| 50 | —(CH₂)₄CH₃.fumarate | 145–149 | C₂₀H₃₀N₂O₅ | C 63.47<br>H 7.99<br>N 7.41 | C 63.37<br>H 7.82<br>N 7.31 |
| 51 | —(CH₂)₆CH₃.fumarate | 130–136 | C₂₂H₃₄N₂O₅ | C 65.00<br>H 8.43<br>N 6.89 | C 64.72<br>H 8.50<br>N 6.80 |
| 52 | —(CH₂)₇CH₃.2HCl | 176–184 | C₁₉H₃₄N₂OCl₂ | C 60.47 | C 60.69 |

TABLE 5-continued

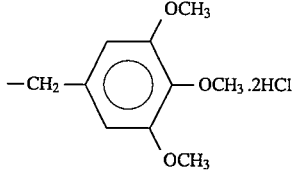

| Ex. No. | R.Salt | m.p. (°C.) | Exp. formula | Calcd. | Found |
|---|---|---|---|---|---|
|  |  |  |  | H 9.08<br>N 7.42 | H 9.11<br>N 7.40 |
| 53 | —(CH₂)₈CH₃.fumarate | 127–137 | C₂₄H₃₈N₂O₅ | C 66.33<br>H 8.81<br>N 6.45 | C 66.22<br>H 8.72<br>N 6.15 |
| 54 | —CH₂—(3,4,5-trimethoxyphenyl).2HCl | 195–199 | C₂₁H₃₀N₂O₄Cl₂ | C 56.63<br>H 6.79<br>N 6.29 | C 56.44<br>H 6.83<br>N 6.51 |
| 55 | —CH₂—Ph.2HCl | 155–164 | C₁₈H₂₄N₂OCl₂ | C 60.85<br>H 6.81<br>N 7.88 | C 60.75<br>H 6.96<br>N 7.71 |
| 56 | —CH₂CH=CH—Ph.2HCl | 175–186 | C₂₀H₂₆N₂OCl₂ | C 62.99<br>H 6.87<br>N 7.35 | C 63.14<br>H 6.95<br>N 7.12 |
| 57 | —cyclohexyl.2HCl | 191–204 | C₁₇H₂₈N₂OCl₂ | C 58.79<br>H 8.13<br>N 8.07 | C 58.53<br>H 8.40<br>N 8.22 |
| 58 | —cyclopentyl.fumarate | 146–151 | C₂₀H₂₈N₂O₅ | C 63.81<br>H 7.50<br>N 7.44 | C 63.73<br>H 7.68<br>N 7.53 |
| 59 | —CH(CH₃)(CH₂)₈CH₃.2HCl | 171–182 | C₂₂H₄₀N₂OCl₂ | C 62.99<br>H 9.61<br>N 6.68 | C 63.05<br>H 9.81<br>N 6.43 |
| 60 | —CH(Ph)(CH₂)₈CH₃.2HCl | 154–165 | C₂₇H₄₄N₂OCl₂ | C 67.34<br>H 8.79<br>N 5.82 | C 67.57<br>H 8.83<br>N 5.81 |
| 61 | —(CH₂)₉OH.2HCl | 139–145 | C₂₀H₃₆N₂O₂Cl₂ | C 58.96<br>H 8.91<br>N 6.88 | C 58.84<br>H 8.79<br>N 6.97 |
| 62 | —(CH₂)₉COOH.2HCl | 138–143 | C₂₁H₃₆N₂O₃Cl₂ | C 57.93<br>H 8.33<br>N 6.43 | C 58.16<br>H 8.59<br>N 6.32 |

TABLE 6

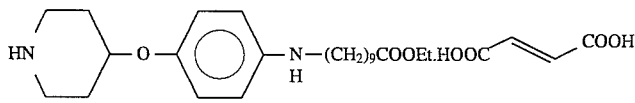

| Ex. No. | R.Salt | m.p. (°C.) | Exp. formula | Calcd. | Found |
|---|---|---|---|---|---|
| 63 | CH₃ —⟨ (CH₂)₃CH₃ .fumarate | 94–97 | C₂₂H₃₄N₂O₅ | C 65.00 H 8.43 N 6.89 | C 65.23 H 8.42 N 7.09 |
| 64 | CH₂CH₃ —⟨ (CH₂)₃CH₃ .fumarate | 111–113 | C₂₃H₃₆N₂O₅ | C 65.68 H 8.63 N 6.66 | C 65.89 H 8.57 N 6.69 |
| 65 | (CH₂)₃CH₃ —⟨ (CH₂)₃CH₃ .fumarate | 127–134 | C₂₅H₄₀N₂O₅ | C 66.93 H 8.99 N 6.25 | C 66.84 H 8.72 N 6.48 |
| 66 | Ph —⟨ (CH₂)₃CH₃ .2HCl | 157–166 | C₂₃H₃₄N₂OCl₂ | C 64.93 H 8.06 N 6.58 | C 64.67 H 7.90 N 6.44 |

EXAMPLE 67

4-[4-(9-Ethoxycarbonylamino)phenyloxy]piperidine fumarate

Ethanol (5 ml) was cooled in a dry ice-acetone bath and thionyl chloride (0.3 ml) was added dropwise. To this solution was added a solution of the compound of Example 62 (1.7 g) in ethanol (5 ml). The mixture was allowed to warm to room temperature and heated under reflux for 2 hours. The reaction mixture was concentrated and to the residue was added methylene chloride (50 ml). The mixture was washed with aqueous saturated solution of sodium bicarbonate, the organic layer was separated and dried over anhydrous sodium sulfate and the solvent was distilled off. The residue was dissolved in ethanol (20 ml) and to the solution was added fumaric acid (0.40 g). The solvent was distilled off to leave a solid. The solid was recrystallized from ethanol to obtain white crystals (1.6 g), m.p. 133°–139° C.

Elemental analysis, Calcd. for C₂₇H₄₂N₂O₇: C, 64.01; H, 8.36; N, 5.53 Found: C, 64.19; H, 8.27; N, 5.44

EXAMPLE 68

1-tert-Butyloxycarbonyl-4-(4-hexylaminophenyloxy) piperidine

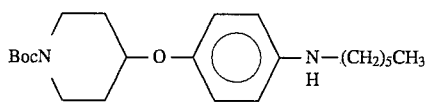

According to the same manner as that described in Example 30, colorless crystals having m.p. of 46°–47° C. was obtained by using 1-tert-butyloxycarbonyl-4-(4-aminophenyloxy)piperidine.

Elemental analysis, Calcd. for C₂₂H₃₆N₂O₃: C, 70.17; H, 9.64; N, 7.44 Found: C, 69.96; H, 9.48; N, 7.38

EXAMPLE 69

4-(4-Hexylaminophenyloxy)-1-methylpiperidine dihydrochloride

To a solution of the compound of Example 68 (1.5 g) in tetrahydrofuran (20 ml) was added lithium aluminum hydride (0.15 g) and the mixture was heated under reflux for hours. Water was added to the mixture and the precipitate formed was filtered off and the filtrate was concentrated. The residue was purified by silica gel column chromatography (developing solvent: methylene chloride/methanol=10/1 (v/v)) to obtain 4-(4-hexylaminophenyloxy)-1-methylpiperidine (0.92 g) as a brown oil. The oil was dissolved in ethanol (20 ml), conc. hydrochloric acid (0.53 ml) was added to the solution and the solvent was distilled off to leave a solid. The solid was recrystallized from ethanol/ethyl ether to obtain 4-(4-hexylaminophenyloxy)-1-methylpiperidine dihydrochloride (0.76 g) as white crystals, m.p. 163°–172° C.

Elemental analysis, Calcd. for $C_{18}H_{32}N_2OCl_2$: C, 59.50; H, 8.88; N, 7.71 Found: C, 59.76; H, 8.94; N, 7.49

EXAMPLE 70

4-(4-Hexylaminophenyloxy)-1-ethylpiperidine dihydrochloride

According to the same manner as that described in Example 69, 4-(4-hexylaminophenyloxy)-1-ethylpiperidine dihydrochloride (0.62 g) was obtained by using the compound of Example 32 (0.98 g) as a non-crystalline solid.

Elemental analysis, Calcd. for $C_{19}H_{34}N_2OCl_2$: C, 60.47; H, 9.08; N, 7.42 Found: C, 60.35; H, 9.32; N, 7.20

NMR ($D_2O$) δ: 0.78–0.85 (3H, m), 1.20–1.38 (9H, m), 1.58–1.73 (2H, m), 1.84–2.43 (4H, m), 3.02–3.69 (8H, m), 7.14, 7.15 (total 2H, each in 1:2 ratio, J–9.0 Hz), 7.40 (2H, d, J=9.0 Hz)

EXAMPLE 71

4-[4-(10-hydroxydecyl)aminophenyloxy]piperidine fumarate

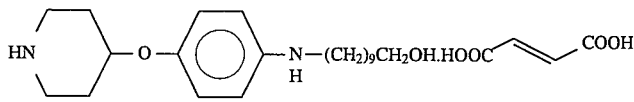

To a solution of the compound of Example 67 from which the acid addition salt was removed (0.85 g) in tetrahydrofuran (30 ml) was added lithium aluminum hydride (85 mg) and the mixture was heated under reflux for 1 hour. The precipitate formed was filtered off and the filtrate was concentrated. The residue was dissolved in ethanol (20 ml) and fumaric acid (280 mg) was added to the solution. The solvent was distilled off and the residual solid was recrystallized from ethanol to obtain 4-[4-(10-hydroxydecyl)aminophenyloxy]piperidine fumarate as light brown crystals, m.p. 139°–143° C.

Elemental analysis, Calcd. for $C_{25}H_{39}N_2O_6$: C, 64.77; H, 8.48; N, 6.04 Found: C, 64.58; H, 8.55; N, 6.00

EXAMPLE 72

4-(4-Hexylaminophenyloxy)-1-phenylmethylpiperidine dihydrochloride

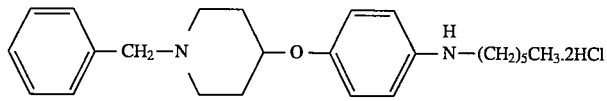

(1) To a solution of the compound of Example 68 (11.3 g) in methylene chloride (50 ml) were added triethylamine (8.4 ml) and acetyl chloride (2.4 g) with icecooling. The mixture was allowed to warm to room temperature and stirred for 2 hours. Aqueous saturated solution of sodium bicarbonate was added to the reaction mixture and the organic layer was separated. The aqueous layer was further extracted with methylene chloride (50 ml×2). The combined extract was dried over anhydrous sodium sulfate and the solvent was distilled off to obtain 1-tert-butyloxycarbonyl-4-(N-acetyl-N-hexylaminophenyloxy)piperidine (12.5 g) as a brown oil.

(2) Trifluoroacetic acid (25 ml) was added to 1-tert-butyloxycarbonyl-4-(N-acetyl-N-hexylaminophenyloxy)piperidine (12.5 g) with ice-cooling and the mixture was stirred at room temperature for 1 hour. The reaction mixture was concentrated and methylene chloride (50 ml) was added to the residue and the mixture was washed with aqueous saturated solution of sodium bicarbonate. The aqueous layer was extracted with methylene chloride (50 ml×3), the combined organic layer were dried over anhydrous sodium sulfate and the solvent was distilled off to obtain 4-(N-acetyl-N-hexylaminophenyloxy)piperidine (9.7 g) as a brown oil.

(3) To a solution of 4-(N-acetyl-N-hexylaminophenyloxy)piperidine (1.4 g) in ethanol (10 ml) were added potassium carbonate (1.2 g) and benzyl chloride (0.54 g) and the mixture was heated under reflux overnight. Water was added to the reaction mixture, which was extracted with ethyl acetate (50 ml×3). The combined extract was dried over anhydrous sodium sulfate and the solvent was distilled off. The residue was purified by silica gel column chromatography (developing solvent: methylene chloride/methanol =10/1 (v/v)) to obtain 4-(N-acetyl-N-hexylaminophenyloxy)-1-phenylmethylpiperidine (1.2 g) as a pale yellow oil.

NMR (CDCl$_3$) δ: 0.82–0.88 (3H, m), 1.25 (6H, m), 1.40–1.52 (2H, m), 1.80 (3H, s), 1.75–2.08 (4H, m), 2.32 (2H, ddd, J=3.4, 8.8, 11.4 Hz), 2.76 (2H, ddd, J=3.8, 5.8, 11.4 Hz), 3.54 (2H, s), 3.63 (2H, t, J=7.6 Hz), 4.26–4.36 (1H, m), 6.90 (2H, d, J=9.0 Hz), 7.03 (2H, d, J=9.0 Hz), 7.27–7.34 (5H, m)

(4) According to the same manner as that described in Example 5, 4-(N-acetyl-N-hexylaminophenyloxy)-1-phenylmethylpiperidine (0.5 g) was subjected to deacetylation to obtain colorless crystals (0.41 g), m.p. 187°–197° C.

Elemental analysis, Calcd. for $C_{24}H_{36}C_{12}N_2O$: C, 65.59; H, 8.26; N, 6.37 Found: C, 65.79; H, 8.48; N, 6.35

EXAMPLES 73 and 74

According to the same manner as that described in Example 72, the compounds as shown in Table 7 were obtained.

TABLE 7

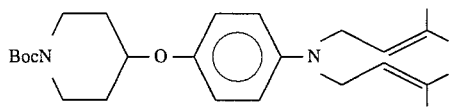

| Ex. No. | R | Salt | m.p. (°C.) | Exp. formula | Elemental analysis Calcd. | Found |
|---|---|---|---|---|---|---|
| 73 | —$CH_2CH_2Ph$ | 2HCl | 167–176 | $C_{25}H_{38}N_2OCl_2$ | C 66.21<br>H 8.54<br>N 6.18 | C 65.98<br>H 8.39<br>N 6.21 |
| 74 | —$CHPh_2$ | fumarate | 76–82 | $C_{34}H_{39}N_2O_5$ | C 73.09<br>H 7.58<br>N 5.01 | C 73.30<br>H 7.38<br>N 4.78 |

EXAMPLE 75

1-tert-Butyloxycarbonyl-4-[4-[N,N-bis(3-methyl-2-butenyl)amino]phenyloxy]piperidine To a solution of 1-tert-butyloxycarbonyl-4-(4-aminophenyloxy)piperidine (1.0 g) obtained in Example 12, (2) in ethanol were added potassium carbonate (0.84 g) and 3-methyl-2-butenyl bromide (0.58 g) and the mixture was stirred at room temperature overnight. Water was added to the reaction mixture and the mixture was extracted with methylene chloride (50 ml×2). The combined organic layer was washed with saturated saline, dried over anhydrous sodium sulfate and concentrated under reduced pressure. The residue was purified by silica gel column chromatography (developing solvent: hexane/ethyl acetate=10/1 (v/v)) to obtain 1-tert-butyloxycarbonyl-4-[N,N-bis(3-methyl-2butenyl)aminophenyloxy]piperidine (0.73 g) as a coloress oil.

Elemental analysis, Calcd. for $C_{26}H_{40}N_2O_3$: C, 72.86; H, 9.41; N, 6.54 Found: C, 72.59; H, 9.38; N, 6.41

NMR (CDCl$_3$) δ: 1.46 (9H, s), 1.62–1.98 (4H, m), 1.67 (6H, s), 1.71 (6H, s), 3.26 (2H, ddd, J=3.6, 7.6, 13.6 Hz), 3.66–3.79 (6H, m), 4.21–4.31 (1H, m), 5.17–5.23 (2H, m), 6.66 (2H, d, J=9.0 Hz), 6.81 (2H, d, J=9.0 Hz)

EXAMPLE 76

4-[4-[N,N-Bis(3-methyl-2-butenyl)amino]phenyloxy]-piperidine fumarate

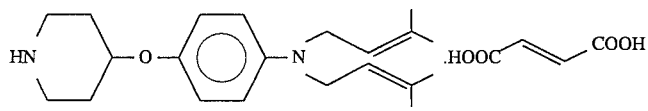

According to the same manner as that described in Example 72, (2), 4-[4-[N,N-bis(3-methyl-2-butenyl)amino]phenyloxy]piperidine fumarate (0.45 g) as light brown crystals having m.p. of 117°–120° C. was obtained from the compound of Example 75 (0.65 g).

EXAMPLE 77

4-[4-(3-Methyl-2-butenyl)aminophenyloxy]piperidine ½ fumarate

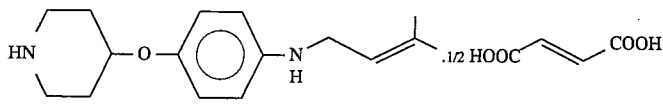

(1) According to the same manner as that described in Example 12, (1), 1-tert-butyloxycarbonyl-4-(4-tertbutyloxy-carbonylaminopehnyloxy)piperidine (3.3 g) as white crystals having m.p. of 154°–156° C. was obtained from 1-tert-butyloxy-carbonyl-4-(4-aminophenyloxy)piperidine (3.0 g) in Example 12 (2).

(2) To a solution of 1-tert-butyloxycarbonyl-4-(4-tert-butyloxycarbonylaminophenyloxy)piperidine (0.9 g) in acetone (20 ml) were added solid potassium hydroxide (0.13 g) and 3-methyl-2-butenyl bromide (0.34 g) and the mixture was heated under reflux overnight. Water was added to the reaction mixture and the mixture was extracted with methylene chloride (50 ml×3). The combined organic layer was dried over anhydrous sodium sulfate and the solvent was distilled off. The resulting residue was purified by silica gel column chromatography (developing solvent: hexane/ethyl acetate=4/1 (v/v)) to obtain 1-tert-butyloxycarbonyl-4-[4[N-tert-butyloxycarbonyl-N-(3-methyl-2-butenyl)amino]-phenyloxy]piperidine (0.23 g) as a colorless oil.

NMR (CDCl$_3$) δ: 1.43 (9H, s), 1.47 (9H, s), 1.51 (3H, s), 1.69 (3H, s), 1.71–1.96 (4H, m), 3.32 (2H, ddd, J=4.0, 7.8, 13.6 Hz), 3.70 (2H, ddd, J=4.0, 7.4, 13.6 Hz), 4.14 (2H, d, J=7.0 Hz), 4.42 (1H, m), 5.26 (1H, m), 6.83 (2H, d, J=9.0 Hz), 7.08 (2H, d, J=9.0 Hz)

(3) According to the same manner as that described in Example 14, colorless crystals (0.12 g) having m.p. of 145°–148° C. were obtained from the above 1-tert-butyloxycarbonyl-4-[4-[N-tert-butyloxycarbonyl-N-(3-methyl-2-butenyl)amino]phenyloxy]piperidine (0.2 g).

Elemental analysis, Calcd. for C$_{18}$H$_{26}$N$_2$O$_3$: C, 67.89; H, 8.23; N, 8.80 Found: C, 67.63; H, 8.18; N, 8.97

EXAMPLE 78

1-Acetyl-4-(2-piperidin-1-ylphenyloxy)piperidine hydrochloride

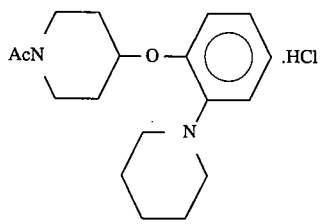

(1) According to the same manner as that described in Example 1, (1), 1-acetyl-4-(2-nitrophenyloxy)piperidine (4.0 g) as a brown oil was obtained from 1-acetyl-4-hydroxypiperidine (3.0 g) and o-fluoronitrobenzene (3.3 g).

(2) According to the same manner as that described in Example 1, (2), 1-acetyl-4-(2-nitrophenyloxy)piperidine (4.0 g) was subjected to catalytic reduction to obtain 1-acetyl-4-(2-aminophenyloxy)piperidine (3.4 g) as a brown oil. This was dissolved in dimethylformamide (20 ml) and to the solution were added dibromopentane (3.6 g) and potassium carbonate (5.8 g). The mixture was heated to 100° C. and stirred overnight. Water was added and the mixture was extracted with ethyl acetate (50 ml×3). The organic layer was dried over anhydrous sodium sulfate and concentrated under reduced pressure. The residue was dissolved in ethanol (30 ml), conc. hydrochloric acid (1.2 ml) was added thereto and the solvent was distilled off. The solid obtained was recrystallized from ethanol/ethyl ether to obtain 1-acetyl-4-(2-piperidin-1-ylphenyloxy)piperidine (4.9 g) as brown crystals, m.p. 69°–70° C.

Elemental analysis, Calcd. for C$_{18}$H$_{27}$N$_2$O$_2$Cl: C, 63.80; H, 8.03; N, 8.27 Found: C, 63.62; H, 8.07; N, 8.04

EXAMPLE 79

1-Acetyl-4-(3-piperidin-1-ylphenyloxy)piperidine hydrochloride

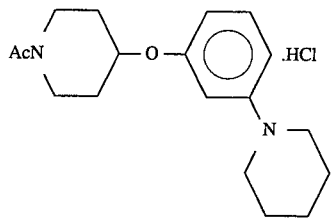

(1) According to the same manner as that described in Example 1, (1), 1-acetyl-4-(3-nitrophenyloxy)piperidine (2.1 g) as a brown oil was obtained from 1-acetyl-4-hydroxypiperidine (3.0 g) and m-fluoronitrobenzene (3.3 g).

(2) According to the same manner as that described in Example 1, (2), 1-acetyl-4-(3-nitrophenyloxy)piperidine (2.0 g) was subjected to catalytic reduction to obtain 1-acetyl-4-(3-aminophenyloxy)piperidine (2.0 g) as a brown oil. The oil and dibromopentane (2.2 g) were reacted according to the same manner as that described in Example 78, (2) to obtain 1-acetyl-4-(3-piperidin-1-ylphenyloxy)piperidine hydrochloride (2.3 g) as a brown amorphous material.

Elemental analysis, Calcd. for C$_{18}$H$_{27}$N$_2$O$_2$Cl: C, 63.80; H, 8.03; 8.27 Found: C, 63.91; H, 8.11; N, 8.14

NMR (D$_2$O) δ: 1.67, 1.92 (total 10 H, brm), 2.04 (3H, s), 3.33–3.72 (8H, m), 4.66(1H, m), 7.05–7.14, 7.39–7.47 (total 4H, m)

EXAMPLE 80

4-(2-Piperidin-1-ylphenyloxy)piperidine ½ fumarate

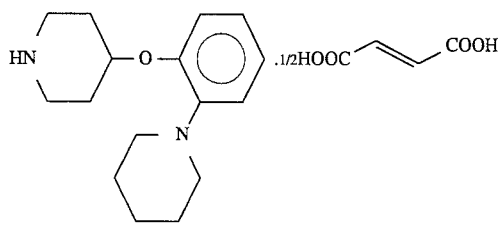

According to the same manner as that described in Example 5, 4-(2-piperidin-1-ylphenyloxy)piperidine ½ fumarate (0.94 g) as gray crystals having m.p. of 175°–199° C. was obtained from the compound of Example 78 (2.8 g).

Elemental analysis, Calcd. for $C_{18}H_{26}N_2O_3$: C, 67.89; H, 8.23; N, 8.80 Found: C, 67.64; H, 8.27; N, 8.68

EXAMPLE 81

4-(3-piperidin-1-ylphenyloxy)piperidine dihydorchloride

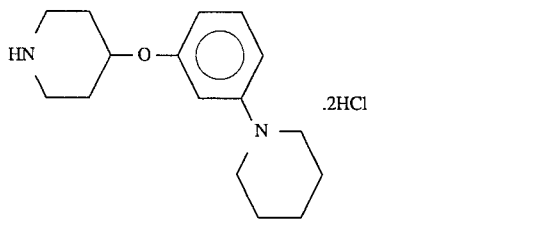

According to the same manner as that described in Example 8, 4-(3-piperidine-1-ylphenyloxy)piperidine dihydrochloride (0.53 g) as light brown crystals having m.p. of 220°–223° C. was obtained form the compound of Example 79 (1.3 g).

Elemental analysis, Calcd. for $C_{16}H_{26}N_2OCl_2$: C, 57.66; H, 7.86; N, 8.40 Found: C, 57.43; H, 7.80; N, 8.38

EXAMPLES 82–86

According to the same manner as that described in Example 12, the compounds shown in Table 8 were obtained.

TABLE 8

| Ex. No. | R | Salt | m.p. (°C.) | Exp. formula | Elemental analysis Calcd. | Found |
|---|---|---|---|---|---|---|
| 82 | $-CH_2CH_3$ | fumarate | 158–162 | $C_{17}H_{24}N_2O_5$ | C 60.70<br>H 7.19<br>N 8.33 | C 60.57<br>H 7.23<br>N 8.09 |
| 83 | $-(CH_2)_3CH_3$ | fumarate | 136–141 | $C_{19}H_{28}N_2O_5$ | C 62.62<br>H 7.74<br>N 7.69 | C 62.43<br>H 7.83<br>N 7.54 |
| 84 | $-(CH_2)_5CH_3$ | fumarate | 115–121 | $C_{21}H_{32}N_2O_5$ | C 64.26<br>H 8.22<br>N 7.14 | C 64.33<br>H 8.42<br>N 7.38 |
| 85 | $-(CH_2)_9CH_3$ | ½ fumarate | 120–127 | $C_{27}H_{42}N_2O_7$ | C 64.01<br>H 8.36<br>N 5.53 | C 64.26<br>H 8.21<br>N 5.43 |
| 86 | $-(CH_2)_{15}CH_3$ | ½ fumarate | 128–135 | $C_{29}H_{50}N_2O_3$ | C 73.37<br>H 10.62<br>N 5.90 | C 73.42<br>H 10.44<br>N 5.71 |

Preparation 1

| | |
|---|---|
| (1) 4-(4-Pentylaminophenyloxy)piperidine fumarate (the compound of Example 50) | 50 g |
| (2) Lactose | 198 g |

-continued

| | |
|---|---|
| (3) Corn starch | 50 g |
| (4) Magnesium stearate | 2 g |

The components (1) and (2) and corn starch (20 g) were admixed and the mixture was granulated with a paste prepared from corn starch (15 g) and water (25 ml). To this was added corn starch (15 g) and the component (4) and the resulting mixture was compressed to produce 1000 tablets of mm in diameter containing the component (1) in an amount of 50 mg per one tablet.

Preparation 2

4-(4-Pentylaminophenyloxy)piperidine fumarate (2 g) and mannitol (1.25 g) were dissolved in a water, pH was adjusted to 5 to 7 with 0.1N NaOH and the total volume of the solution was made up to 100 ml. The solution thus obtained was sterilized by filtration through a filter of 0.2 μ. This was distributed into one hundred of 1 ml-ampoules.

Preparation 3

| | |
|---|---|
| (1) 4-[(4-Pyrrolidinophenyloxyl)methyl]-piperidine fumarate (the compound of Example 16) | 50 g |
| (2) Lactose | 198 g |
| (3) Corn starch | 50 g |
| (4) Magnesium stearate | 2 g |

The components (1) and (2) and corn starch (20 g) were admixed and the mixture was granulated with a paste prepared from corn starch (15 g) and water (25 ml). To this was added corn starch (15 g) and the component (4) and the resulting mixture was compressed to produce 1000 tablets of 5 nun in diameter containing the component (1) in an amount of 50 mg per one tablet.

Preparation 4

4-[(4-Pyrrolidinophenyoxy)methyl]piperidine fumarate (the compound of Example 16, 2 g) and mannitol (1.25 g) were dissolved in water, pH was adjusted to 5 to 7 with 0.1N NaOH and the total amount of the solution was made up to 100 ml. The solution thus obtained was sterilized by filtration through a filter of 0.2 u. This was distributed into one hundred of 1 ml-ampoules.

Experiment

Protective activity to glutamic acid-induced necrocytosis in $N_{18}$-RE-105 cells When a high concentration of glutamic acid (1 to 10 mM) is added to $N_{18}$-RE-105 cells, neocrocytosis caused by oxidative stress due to inhibition of incorporation of cystine into cells is observed [Neuron 2, 1547 (1989); J. Pharmacol. Exp. Ther. 250, 1132 (1989)].

Activity of various compounds against this glutamic acid-induced necrocytosis was studied. About 10,000 cells were inoculated into a culture dish of 35 mm in diameter containing DMEM medium (1 ml). After cultivation for 24 hours, glutamic acid and a compound to be tested were added. After the medium was changed to DMEM mediums containing the compound in various concentrations and then glutamic acid (10 mM) was added. After addition of glutamic acid, cultivation was further continued for 24 hours. Then, surviving cells were collected and lactose dehydration enzyme (LDE) activity contained in the cells and medium was determined. A cell lethal ratio (%) was calculated according to the following formula:

Cell lethal ratio (%) =

$$\frac{LDH \text{ activity in medium}}{LDH \text{ activity in cells} + LDH \text{ activity in medium}} \times 100$$

Regarding the typical compounds of the present invention, minimum concentrations for depressing cell lethal ratio to not more than 50% ($IC_{50}$) is shown in Table 9.

TABLE 9

Effect on glutamic acid cytotoxicity
(cell lethal ratio)

| Example No. | $IC_{50}$ (nM) |
|---|---|
| 5 | 300 |
| 7 | 3000 |
| 15 | 10 |
| 16 | 0.8 |
| 25 | 1.1 |
| 26 | 2.5 |
| 28 | 1.6 |
| 29 | 10 |
| 50 | 10 |
| 51 | 8 |
| 52 | 5.5 |
| 53 | 1.1 |
| 56 | 6.4 |
| 60 | 10 |
| 61 | 6.4 |

As seen from Table 9, the compounds (I) of the present invention or salts thereof strongly inhibit necrosytosis due to glutamic acid.

What is claimed is:

1. A method for inhibiting degeneration and necrocytosis of cerebral nerve cells caused by oxidative stress inducing glutamic acid in mammals which comprises administering to a mammal suffering therefrom a therapeutically effective amount of a compound of the formula (I):

wherein

A and B are independently a group of the formula:

wherein $R_1$ and $R_2$ are independently (i) a hydrogen atom, (ii) a $C_{1-6}$ alkyl, $C_{2-4}$ alkenyl or $C_{2-4}$ alkynyl group which may be substituted by 1 to 4 substituents selected from the group consisting of a halogen, $C_{1-3}$ alkoxy, a cyano, an amino, a mono- or di-$C_{1-6}$ alkylamino, a 5- to 7-membered cyclic amino and a hydroxyl, (iii) a $C_{6-12}$ aryl or $C_{7-14}$ aralkyl group which may be substituted by 1 to 3 substituents on the rings selected from the group consisting of a $C_{1-3}$ alkoxy, a $C_{1-3}$ alkyl, a cyano, an amino, a mono- or di-$C_{1-6}$ alkylamino, a 5- to 7-membered cyclic amino, a hydroxyl, a nitro and a halogen, (iv) a 5- to 8-membered saturated or unsaturated heterocyclic group whose ring-constituting atoms consist of 1 to 4 hetero atoms selected from the group consisting of nitrogen, oxygen, and sulfur which may be substituted by 1 to 3 substituents on the rings selected from the group consisting of a $C_{1-3}$ alkoxy, a $C_{1-3}$ alkyl, a cyano, an amino, a mono- or di-$C_{1-6}$ alkylamino, 5- to 7-membered cyclic amino, a hydroxyl, a nitro, and a halogen, or (v) $R_1$ taken together with $R_2$ and the nitrogen atom to which they are bound may form a group of the formulas:

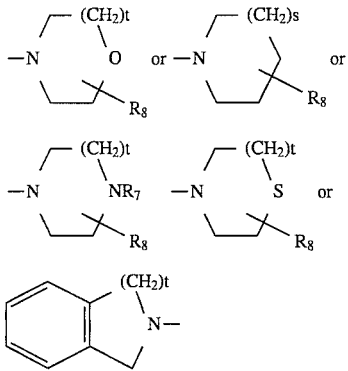

wherein s is 0, 1 or 2;

t is 1 or 2;

$R_7$ is a hydrogen atom or $C_{1-6}$ alkyl group; and $R_8$ is a $C_{1-3}$ alkyl group, a $C_{1-3}$ alkylcarbonyl group, an oxo, a hydroxy group, a phenyl group, a benzyl group, a diphenylmethyl group, an amino group or a hydrogen atom, provided that both $R_1$ and $R_2$ are not hydrogen at the same time, p is 1 or 2, provided that both A groups may be the same or different when p is 2; and $R_4$, $R_5$ and $R_6$ are independently a hydrogen atom, a $C_{1-6}$ alkyl group or a $C_{1-6}$ alkoxy group, or $R_5$ and $R_6$ may bond together to form —CH=CH—CH=CH—, or a pharmaceutically acceptable salt thereof.

2. A method according to claim 1, wherein A and B are

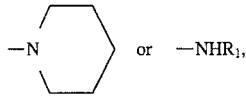

wherein $R_1$ is an alkyl group having 1 to 6 carbon atoms.

3. A method according to claim 2, wherein A is

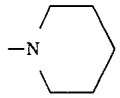

and $R_1$ is $(CH_3)_2CH(CH_2)_3$.

4. A method according to claim 1, wherein the effective component is N-[4-(4-methylpentylamino)phenyl]-piperidine or a pharmaceutically acceptable salt thereof.

* * * * *